US011591409B2

(12) United States Patent
Liu et al.

(10) Patent No.: US 11,591,409 B2
(45) Date of Patent: Feb. 28, 2023

(54) ANTI-PD-L1/ANTI-PD-1 NATURAL ANTIBODY STRUCTURE-LIKE HETERODIMERIC BISPECIFIC ANTIBODY AND PREPARATION THEREOF

(71) Applicant: BEIJING HANMI PHARM. CO., LTD., Beijing (CN)

(72) Inventors: Jiawang Liu, Shunyi District (CN); Nanmeng Song, Shunyi District (CN); Yaping Yang, Shunyi District (CN); Mengxie Jin, Shunyi District (CN)

(73) Assignee: BEIJING HANMI PHARM. CO., LTD., Beijing (CN)

( * ) Notice: Subject to any disclaimer, the term of this patent is extended or adjusted under 35 U.S.C. 154(b) by 439 days.

(21) Appl. No.: 16/498,223

(22) PCT Filed: Mar. 28, 2018

(86) PCT No.: PCT/CN2018/080858
§ 371 (c)(1),
(2) Date: Feb. 24, 2020

(87) PCT Pub. No.: WO2018/177324
PCT Pub. Date: Oct. 4, 2018

(65) Prior Publication Data
US 2020/0299412 A1 Sep. 24, 2020

(30) Foreign Application Priority Data

Apr. 1, 2017 (CN) .......................... 201710214705.7

(51) Int. Cl.
*C07K 16/46* (2006.01)
*C07K 16/30* (2006.01)
*A61K 38/00* (2006.01)

(52) U.S. Cl.
CPC ............ *C07K 16/468* (2013.01); *C07K 16/30* (2013.01); *A61K 38/00* (2013.01); *C07K 2317/14* (2013.01); *C07K 2317/31* (2013.01); *C07K 2317/56* (2013.01)

(58) Field of Classification Search
None
See application file for complete search history.

(56) References Cited

U.S. PATENT DOCUMENTS

| 5,731,168 | A | 3/1998 | Carter et al. |
| 9,562,109 | B2 | 2/2017 | Von Kreudenstein et al. |
| 9,732,155 | B2 | 8/2017 | Spreter Von Kreudenstein et al. |
| 9,758,805 | B2 | 9/2017 | De Kruif et al. |
| 10,344,050 | B2 | 7/2019 | Gramer et al. |
| 2006/0074225 | A1* | 4/2006 | Chamberlain ......... C07K 16/44 530/387.1 |
| 2015/0203579 | A1 | 7/2015 | Papadopoulos et al. |
| 2015/0210769 | A1 | 7/2015 | Freeman et al. |
| 2019/0010232 | A1 | 1/2019 | Kalos et al. |
| 2019/0284299 | A1* | 9/2019 | Liu ....................... C07K 16/32 |

FOREIGN PATENT DOCUMENTS

| CN | 103429620 | A | 12/2013 |
| CN | 104080811 | A | 10/2014 |
| CN | 104114579 | A | 10/2014 |
| CN | 104520320 | A | 4/2015 |
| EP | 3652216 | A1 | 5/2020 |
| JP | 2014504265 | A | 2/2014 |
| JP | 2014523401 | A | 9/2014 |
| JP | 2014530891 | A | 11/2014 |
| JP | 2014533243 | A | 12/2014 |
| JP | 2015514417 | A | 5/2015 |
| JP | 2016510216 | A | 4/2016 |
| JP | 2017505125 | A | 2/2017 |
| JP | 2017506067 | A | 3/2017 |
| WO | WO-2009/089004 | A1 | 7/2009 |
| WO | WO-2012/058768 | A1 | 5/2012 |
| WO | WO-2012145493 | A1 | 10/2012 |
| WO | WO-2013/060867 | A2 | 5/2013 |
| WO | WO-2013063702 | A1 | 5/2013 |
| WO | WO-2016207312 | A1 | 12/2016 |
| WO | WO-2016208695 | A1 | 12/2016 |
| WO | WO-2018/059502 | A1 | 4/2018 |

OTHER PUBLICATIONS

Gunasekaran et al (JBC, 285(25):19637-19646, 2010 and supplementary infomation).*
"European Application No. 18777419.5, Extended European Search Report dated Dec. 7, 2020", (Dec. 7, 2020), 14 pgs.
Brinkmann, Ulrich, "The making of bispecific antibodies", MABS, vol. 9, No. 2, (Jan. 10, 2017), 182-212.
Ha, Ji-Hee, "Immunoglobulin Fc Heterodimer Platform Technology: From Design to Applications in Therapeutic Antibodies and Proteins", Frontiers in Immunology, vol. 7, (Oct. 6, 2016), 1-16.
Hartkopf, Andreas D., et al., "PD-1 and PDL1 immune Checkpoint Blockade to Treat Breast Cancer", Breast Care, vol. 11, No. 6, (Jan. 1, 2016), 385-390.
"IMGT/2Dstructure-DB card for INN 9798", © Copyright 1995-2015 IMGT® [online]. [archived on Apr. 25, 2015]. Retrieved from the Internet: <URL: www.imgt.org/3Dstructure-DB/cgi/details.cgi?pdbcode=9798>, (2015), 2 pgs.
"International Application Serail No. PCT/CN2018/080858, International Search Report dated Jun. 21, 2018", (w/ English Translation), 13 pgs.
"International Application Serail No. PCT/CN2018/080858, Written Opinion dated Jun. 21, 2018", (w/ English Translation), 13 pgs.
Afreen, Sehar, et al., "The immunoinhibitory B7-H1 molecule as a potential target in cancer: Killing many birds with one stone", Hematology/Oncology and Stem Cell Therapy, 7(1), (Mar. 2014), 1-17.

(Continued)

*Primary Examiner* — Brad Duffy
(74) *Attorney, Agent, or Firm* — Schwegman Lundberg & Woessner, P.A.

(57) ABSTRACT

Provided are an anti-PD-L1/anti-PD-1 natural antibody structure-like heterodimeric bispecific antibody and a preparation thereof. In particular, provided are a highly stable heterodimeric anti-PD-L1/anti-PD-1 bispecific antibody with characteristics of a natural IgG and without mismatches heavy chain-light chain, and a preparation thereof. The bispecific antibody can bind to both target molecules and is more effective in treating a complex disease.

8 Claims, 13 Drawing Sheets

Specification includes a Sequence Listing.

(56) References Cited

OTHER PUBLICATIONS

Chen, Daniel S., et al., "Molecular Pathways: Next-Generation Immunotherapy—Inhibiting Programmed Death-Ligand 1 and Programmed Death-1", Clinical Cancer Research, 18(24), (2012), :6580-6587.
Chen, Lieping, et al., "Anti-PD-1/PD-L1 therapy of human cancer: past, present, and future", The Journal of Clinical Investigation, 125(9), (Sep. 2015), 3384-3391.
Gianchecchi, Elena, et al., "Recent insights into the role of the PD-1/PD-L1 pathway in immunological tolerance and autoimmunity", Autoimmunity Reviews. 12(11), (Sep. 2013), 1091-1100.
Haas, Cornelia, et al., "Mode of cytotoxic action of T cell-engaging BiTE antibody MT110", Immunobiology, 214(6), (2009), 441-453.
Henick, Brian S., et al., "The PD-1 pathway as a therapeutic target to overcome immune escape mechanisms in cancer", Expert Opinion on Therapeutic Targets, 18(12), (Oct. 2014), 1-14.
Jager, Michael, et al., "Immunomonitoring Results of a Phase II/III Study of Malignant Ascites Patients Treated with the Trifunctional Antibody Catumaxomab (Anti-EpCAM × Anti-CD3)", Cancer Research, 72(1), (2012), 24-32.
James, Ashley M., et al., "Combination Immune Therapies to Enhance Anti-Tumor Responses by NK Cells", Frontiers in Immunology, 4, Article 481, (2013), 1-12.
Kim, Joseph W. et al., "Prospects for Targeting PD-1 and PD-L1 in Various Tumor Types", Oncology (Willston Park),28(11, Suppl. 3), (Nov. 2014), 15-28 (14 pgs.).
Loffler, Anja, et al., "A recombinant bispeci?c single-chain antibody, CD19 X CD3, induces rapid and high lymphoma-directed cytotoxicity by unstimulated T lymphocytes", Blood, 95(6), (2000), 2098-2103.
Motz, Greg T., et al., "Deciphering and Reversing Tumor Immune Suppression", Immunity, 39(1), (2013), 61-73.
Ohaegbulam, Kim C., et al., "Human cancer immunotherapy with antibodies to the PD-1 and PD-L1 pathway", Trends in Molecular Medicine, 21(1), (2015), 24-33.
Pardoll, Drew M., et al., "The blockade of immune checkpoints in cancer immunotherapy", Nature Reviews Cancer, 12(4), (Apr. 2012), 252-264.
Pilotto, Sara, et al., "Immune Checkpoint Inhibitors for Non-small-cell Lung Cancer: Does that Represent a 'New Frontier'?", Anti-Cancer Agents in Medicinal Chemistry, 15(3), (2015), 1-7.
Postow, Michael A., et al., "Immune Checkpoint Blockade in Cancer Therapy", Journal of Clinical Oncology, 33(17), (2015), 1974-1982 (10 pgs.).
"Chinese Application No. 201880021099.X, First Office Action dated Mar. 1, 2022", (Mar. 1, 2022), 16 pgs.
"Japanese Application No. 2020-502753, Notice of Reasons for Refusal dated Jan. 25, 2022", (Jan. 25, 2022), 11 pgs.
"Japanese Application No. 2020-502753, Search Report dated Jan. 11, 2022", (Jan. 11, 2022), 30 pgs.
Jing, Chu-Yu, et al., "Research advancements of the anti-PD-1/PD-L1 therapy in oncotherapy", Fudan University Journal of Medical, 2016, 43(6), (2016), 710-716.
"Chinese Application No. 201880021099.X, Second Office Action dated Aug. 3, 2022", (Aug. 3, 2022), 6 pgs.

* cited by examiner

1. Mixture of anti-PD-L1 half-antibody molecule and anti-PD-1 half-antibody molecule
2. The mixture of anti-PD-L1 half-antibody molecule and anti-PD-1 half-antibody molecule upon oxidization
M. Molecular weight strandards

ANTI-PD-L1/ANTI-PD-1 NATURAL ANTIBODY STRUCTURE-LIKE HETERODIMERIC BISPECIFIC ANTIBODY AND PREPARATION THEREOF

PRIORITY CLAIM TO RELATED APPLICATIONS

This application is a U.S. national stage filing under 35 U.S.C. § 371 from International Application No. PCT/CN2018/080858, filed on 28 Mar. 2018, and published as WO 2018/177324 A1 on 4 Oct. 2018, which claims the benefit under 35 U.S.C. 119 to Chinese Patent Application No. 201710214705.7, filed on 1 Apr. 2017, the benefit of priority of each of which is claimed herein, and which applications and publication are hereby incorporated herein by reference in their entirety.

TECHNICAL FIELD

The present invention relates to an anti-PD-L1/anti-PD-1 natural antibody structure-like heterodimeric bispecific antibody and preparation thereof. Specifically, the present invention provides a highly stable heterodimeric anti-PD-L1/anti-PD-1 bispecific antibody having characteristics of natural IgGs and having no mismatches heavy chain-light chain, and a method of preparing the same.

BACKGROUND

Monoclonal antibodies are highly specific antibodies that act only on a single antigenic epitope and have been widely used in the treatment of numerous diseases, such as cancers, inflammatory and autoimmune diseases, and infectious diseases. However, because of the complexity of diseases, none of such therapeutic molecules exhibits sufficient efficacy when used alone. For example, cancers or inflammatory diseases are often associated with various disease-mediating molecular pathways and interactions of the signaling pathways. Under these circumstances, a single-targeted molecule may not provide optimal therapeutic effects, while the therapeutic effects may be improved by molecules simultaneously blocking multiple targets or multiple sites on a single target. In the meanwhile, dual-targeted therapy using a multi-specific, such as a bispecific, molecule, may simplify the development of new drugs, because such a molecule is a single molecule. Compared with combined administration of a plurality of monospecific molecules, it would be more convenient to both patients and health workers.

Many different formats of bispecific antibodies or bifunctional molecules have been reported in this field. The first bispecific antibody was obtained by chemical methods using bifunctional coupling reagents to link two existing IgG molecules, Fab', or (Fab')2 fragments together. However, such a chemically coupled bispecific antibody has many limitations, such as in the work intensity of production, purification of heterologous conjugates, complexity in the removal of homologous conjugates and original monospecific antibodies or fragments, and low yield.

Another method for producing bispecific antibodies utilizes the technique of hybrid-hybridoma (or quadroma), which is produced by somatic fusion of two hybridoma cell lines that secrete different antibodies. Due to arbitrary pairing of immunoglobulin heavy and light chains, the desired functional bispecific antibody accounts for only one-tenth of the antibody mixture, which complicates the purification process and reduces the production yield.

WO2013060867 describes a method of mass-production of a heterodimeric bispecific antibody, wherein two homodimeric antibodies are reduced firstly in a mixture; then the asymmetric amino acid mutations are introduced into CH3 regions of the two homodimeric antibodies to promote Fab arm exchange between the different antibodies; a stable bispecific antibody is finally formed by oxidization of interchain disulfide bonds of the hinge regions.

WO2009089004 describes a method of preparing a heterodimeric protein, wherein, amino acids at the CH3-CH3 interface are mutated into charged amino acids such that the formation of heterodimer is electrostatically favorable, while the formation of homodimer is electrostatically unfavorable.

U.S. Pat. No. 5,731,168 describes a method of preparing a heterodimer IgG according to a "protuberance-into-cavity" strategy, wherein "protuberances" are constructed by replacing small amino acids at the interface of the CH3 region of a first chain with larger amino acids; at the same time, "cavities" are created by replacing corresponding large amino acids at the CH3 interface of a second chain with smaller amino acids. The protuberance and cavity interaction is favorable to the formation of heterodimeric IgG, but unfavorable to the formation of homodimer.

WO2012058768 describes a method of preparing a stable and highly specific heterodimer IgG. This method combines both negative and positive designs along with techniques of computational structural modeling-guided protein engineering to mutate a plurality of amino acids in the CH3 domain of IgG1, thereby forming a stable heterodimer IgG with a low content of homodimeric impurities.

As an effective means to improve the efficacy of antibodies, a bi-functional antibody capable of recruiting effector cells can be designed. Until now, the utilization of the function of CD3 molecule has been studied most. By activating killer T cells with CD3 molecule, the tumor of interest can be effectively eliminated (Haas C. et al., Immunobiology, 214:441-453, 2009). Among the above, BiTE which is a recombinant bifunctional T cell-stimulating antibody developed by Micromet, Inc., has shown great promise. However, the biggest problem is that its serum half-life is very short and its half-life in the human body is only 1 hour (Loffler A. et al., Blood, 95:2098-2103). This is attributed to BiTE's own structure, which is composed of two single-chain antibody fragments with a molecular weight only 60 kDa, and lacks Fc fragments in antibody molecules, which have significant effects on half-life extension.

Catumaxomab, as another promising multi-functional antibody, is a hybrid Ig molecule targeting CD3 and EpCAM. Currently, this product is approved for the treatment of ascites cancer (Jager M. et al, Cancer Res, 72:24-32, 2012). Still another multi-functional antibody under Phase-II clinical trial is ertumaxomab which targets CD3 and PD-L1. One heavy chain and one light chain of the hybrid antibody are derived from rat IgG and target CD3; another heavy chain and light chain are derived from mouse IgG and target PD-L1. Consequently, there is problem that the production of such product is quite difficult, since a quadroma capable of expressing a bifunctional anti-CD3/anti-PD-L1 antibody is required to obtain the cell line expressing bifunctional ertumaxomab. The quadroma is obtained by firstly obtaining a diploid hybridoma strain expressing CD3 antibody and a diploid hybridoma strain expressing a PD-L1 antibody, and then hybridizing the two hybridoma strains. In contrast, only one diploid hybridoma strain is required for the production of a conventional single-targeted antibody. In comparison therewith, the production process of a bifunctional antibody is more complicated, as it is even more difficult to obtain a quadroma. Moreover, the murine-origin results in its extremely high immunogenicity.

Furthermore, the most obvious side effect caused by anti-CD3 antibody is the burst of cytokines in vivo in a short time, which is also called cytokine storm. Accordingly, there is a need for a novel bifunctional antibody that recruits immune cells to the surface of tumor cells at the same time.

Programmed death receptor-1 (PD-1) is an immune checkpoint that has recently attracted much attention. PD-1 is a member belonging to CD28 family. Unlike other members of the CD28 family, such as CTLA4, capable of forming a covalent dimer via disulfide bond, PD-1 exists in monomeric form. The structure of PD-1 mainly includes an immunoglobulin variable region-like extracellular domain, a hydrophobic transmembrane domain, and an intracellular domain. The intracellular domain contains two independent phosphorylation sites: an immunoreceptor tyrosine-based inhibitory motif (ITIM) and an immunoreceptor tyrosine-based switch motif (ITSM), respectively. PD-1 is mainly inducibly expressed on the surface of activated T cells, and also on B cells, NK cells, monocytes, and DC cells. PD-1 mainly involves in the negative control of T cell activation, and may regulate the strength and duration of immune responses. The ligands of PD-1 include PD-L1 (programmed death ligand 1) and PD-L2 (programmed death ligand 2). These ligands belong to the B7 family. In the above, PD-L1 is inducibly expressed on the surface of various immune cells including T cells, B cells, monocytes, macrophages, DC cells, and endothelial cells, epidermal cells, etc., while PD-L2 is inducibly expressed only on some immune cells, including macrophages, DC cells and B cells. PD-L1 not only acts as a ligand for PD-1, but also acts as a ligand for CD80, transmits negative regulatory signals to T cells and induces immune tolerance of T cells (Autoimmun Rev, 2013, 12(11):1091-1100. Front Immunol, 2013, 4:481. Nat Rev Cancer, 2012, 12(4): 252-264. Trends Mol Med. 2015 January; 21(1): 24-33. Clin Cancer Res. 2012 Dec. 15; 18(24):6580-7).

Under normal circumstances, PD-1 and PD-L1 can mediate and maintain the autoimmune tolerance of organism tissues, prevent immune system from over-activating and impairing self-tissues in the inflammatory processes, and have positive effects on the avoidance of occurrence of autoimmune diseases. Under pathological circumstances, they participate in the tumor immunity, and occurrence and development of various autoimmune diseases. There are several publications report that PD-L1 is highly expressed in various tumor tissues, and PD-1 is highly expressed in tumor-infiltrating lymphocytes. Further, the over-expression of PD-L1 and PD-1 is closely associated with the poor clinical prognosis of tumors (Anticancer Agents Med. Chem. 2015; 15(3):307-13. Hematol Oncol Stem Cell Ther. 2014 March; 7(1):1-17. Trends Mol Med. 2015 January; 21(1):24-33. Immunity. 2013 Jul. 25; 9(1):61-73. T Clin Oncol. 2015 Jun. 10; 33(17):1974-82). Blocking PD-1/PD-L1 and PD-1/PD-L2 with PD-1 mAb, or blocking PD-1/PD-L1 and CD80/PD-L1 with PD-L1 mAb, has shown satisfactory anti-tumor effects in both pre-clinical and clinical trials. At present, PD-1 mAb has been approved by U.S. FDA for the treatment of various tumors, including non-small cell lung cancer, melanoma, head and neck cancer, etc. PD-L1 mAb has also been approved for the treatment of non-small cell lung cancer and urothelial cancer. However, only a small part of tumor patients could benefit from such monoclonal antibody therapy, while most patients do not respond to such monoclonal antibodies (Expert Opin Ther Targets. 2014 December; 18 (12): 1407-20. Oncology (Williston Park). 2014 November; 28 Suppl 3:15-28).

Therefore, it is necessary to develop a novel, more potent, bifunctional antibody that simultaneously blocks PD-1/PD-L1, PD-1/PD-L2 and CD80/PD-L1 and that recruits immune cells to the surface of tumor cells.

SUMMARY OF THE INVENTION

The present invention provides a highly stable heterodimeric bispecific antibody which has the structural characteristics of natural IgGs, has no mismatches heavy chain-light chain, and could block PD-L1 and PD-1 simultaneously, and provides a method of preparing the same. The bifunctional antibody binds simultaneously to PD-L1 expressed on tumor cells and PD-1 expressed on immune cells, thereby exerting highly effective and specific killing effect, and lower toxic and side effects at the same time.

In the first aspect, the present invention relates to a heterodimeric bispecific antibody, comprising a first antigen-binding functional region capable of specifically binding to PD-L1 and a second antigen-binding functional region capable of specifically binding to PD-1, wherein the bispecific antibody comprises a first Fc chain and a second Fc chain linked by one or more interchain disulfide bonds, the first Fc chain and the second Fc chain are linked respectively to the PD-L1 antigen-binding functional region and the PD-1 antigen-binding functional region by a covalent bond or a linker; and the first Fc chain and the second Fc chain comprise 5 amino acid substitutions at the following positions: substitutions of amino acids at positions 366 and 399 on the first Fc chain, and substitutions of amino acids at positions 351, 407 and 409 on the second Fc chain, the first Fc chain and the second Fc chain comprising the above amino acid substitutions tend to form heterodimers with each other, rather than forming respective homodimers, wherein the amino acid positions are numbered according to the Kabat EU index numbering system.

In some embodiments, the amino acid substitutions of the first Fc chain and the second Fc chain are as the followings:
  a) substitution at position 351 with glycine, tyrosine, valine, proline, aspartic acid, glutamic acid, lysine or tryptophan;
  b) substitution at position 366 with leucine, proline, tryptophan or valine;
  c) substitution at position 399 with cysteine, asparagine, isoleucine, glycine, arginine, threonine or alanine;
  d) substitution at position 407 with leucine, alanine, proline, phenylalanine, threonine or histidine;
  e) substitution at position 409 with cysteine, proline, serine, phenylalanine, valine, glutamine or arginine.

In some embodiments, the amino acid substitutions are as the followings:
  a) substitutions of T366L and D399R on the first Fc chain, substitutions of L351E, Y407L and K409V on the second Fc chain;
  b) substitutions of T366L and D399C on the first Fc chain, substitutions of L351G, Y407L and K409C on the second Fc chain;
  c) substitutions of T366L and D399C, on the first Fc chain, substitutions of L351Y, Y407A and K409P on the second Fc chain;
  d) substitutions of T366P and D399N on the first Fc chain, substitutions of L351V, Y407P and K409S on the second Fc chain;

e) substitutions of T366W and D399G on the first Fc chain, substitutions of L351D, Y407P and K409S on the second Fc chain;
f) substitutions of T366P and D399I on the first Fc chain, substitutions of L351P, Y407F and K409F on the second Fc chain;
g) substitutions of T366V and D399I on the first Fc chain, substitutions of L351K, Y407I and K409Q on the second Fc chain;
h) substitutions of T366L and D399A on the first Fc chain, substitutions of to L351W, Y407H and K409R on the second Fc chain.

In some embodiments, the amino acid substitutions on the first Fc chain are T366L and D399R, the amino acid substitutions on the second Fc chain are L351E, Y407L and K409V.

In some embodiments, the Fc chains are derived from IgG.

In some embodiments, the PD-L1 and PD-1 antigen-binding functional regions are Fab fragments or scFv fragments.

In some embodiments, the PD-L1 and PD-1 antigen-binding functional regions are both Fab fragments.

In some embodiments, one of the PD-L1 and PD-1 antigen-binding functional regions is a Fab fragment, and the other is a scFv.

In some embodiments, the Fab fragment comprises a first heavy chain variable region and a second heavy chain variable region, which are different, and a first light chain variable region and a second light chain variable region, which are different.

In some embodiments, the amino acid sequence of the bispecific antibody is selected from the group consisting of SEQ ID NOs: 2, 4, 6, 8, 10, 12, 14, 16, and 18.

In the second aspect, the present invention relates to an isolated polynucleotide, encoding a heterodimeric bispecific antibody according to the first aspect.

In some embodiments, the sequence of the polynucleotide is selected from the group consisting of SEQ ID NOs: 1, 3, 5, 7, 9, 11, 13, 15, and 17.

In the third aspect, the present invention relates to a recombinant expression vector, comprising the isolated polynucleotide according to the second aspect.

In some embodiments, the expression vector is plasmid vector X0GC obtained by engineering based on pCDNA.

In the fourth aspect, the present invention relates to a host cell, comprising the isolated polynucleotide according the second aspect, or the recombinant expression vector according to the third aspect.

In some embodiments, the host cell is selected from human embryonic kidney cell HEK293 or cells obtained by engineering based on HEK293 cells, such as HEK293T, HEK293F, HEK293E; hamster ovary cell CHO or cells obtained by engineering based on CHO cells, such as CHO-S, CHO-dhfr⁻, CHO/DG44, ExpiCHO; *Escherichia coli* or stains obtained by engineering based on *E. coli*, such as BL21, BL21 (DE3), Rosetta, Origami; yeasts or stains obtained by engineering based on yeasts, such as *Pichia pastoris, Saccharomyces cerevisiae, Kluyveromyces cerevisiae, Hansenula polymorpha*; insect cells or cells obtained by engineering based on insect cells, such as High5, SF9; plant cells; mammalian mammary cells, somatic cells and the likes.

In the fifth aspect, the present invention relates to a composition comprising a heterodimeric bispecific antibody according to the first aspect, or an isolated polynucleotide according to the second aspect, or a recombinant expression vector according to the third aspect, or a host cell according to the fourth aspect, and a pharmaceutically acceptable carrier.

In the sixth aspect, the present invention relates to a method for producing a heterodimeric bispecific antibody according to the first aspect, comprising the steps of:
1) separately expressing an isolated polynucleotide according to the second aspect or a recombinant expression vector according to the third aspect in a host cell;
2) reducing the proteins separately expressed in the host cell; and
3) mixing the reduced proteins, and then oxidizing the mixture.

In some embodiments, the host cell is selected from human embryonic kidney cell HEK293 or cells obtained by engineering based on HEK293 cells, such as HEK293T, HEK293F, HEK293E; hamster ovary cell CHO or cells obtained by engineering based on CHO cells, such as CHO-S, CHO-dhfr⁻, CHO/DG44, ExpiCHO; *Escherichia coli* or stains obtained by engineering based on *E. coli*, such as BL21, BL21 (DE3), Rosetta, Origami; yeasts or stains obtained by engineering based on yeasts, such as *Pichia pastoris, Saccharomyces cerevisiae, Kluyveromyces cerevisiae, Hansenula polymorpha*; insect cells or cells obtained by engineering based on insect cells, such as High5, SF9; plant cells; mammalian mammary cells, somatic cells and the likes.

In some embodiments, the reducing step comprises: 1) performing a reduction reaction, wherein the reducing agent is selected from the group consisting of 2-mercaptoethylamine, dithiothreitol, tris(2-carboxyethyl)phosphine or a chemical derivative thereof, or a combination thereof; 2) removing the reducing agent.

In some embodiments, the oxidizing step is oxidization in air, but also comprises performing an oxidation reaction in the presence of an oxidizing agent which is selected from the group consisting of L-dehydroascorbic acid or other chemical derivatives.

In some embodiments, the method further comprises a step of separation and purification.

In the seventh aspect, the present invention relates to use of a heterodimeric bispecific antibody according to the first aspect, and/or an isolated polynucleotide according to the second aspect, and/or a recombinant expression vector according to the third aspect, and/or a host cell according to the fourth aspect, and/or a composition according to the fifth aspect, in manufacture of a medicament for preventing and/or treating a disease in a subject.

In the eighth aspect, the present invention relates to a heterodimeric bispecific antibody according to the first aspect, and/or an isolated polynucleotide according to the second aspect, and/or a recombinant expression vector according to the third aspect, and/or a host cell according to the fourth aspect, and/or a composition according to the fifth aspect, for use as a medicament for preventing and/or treating a disease in a subject.

In the ninth aspect, the present invention relates to a method for preventing and/or treating a disease, comprising administering to a subject in need thereof a heterodimeric bispecific antibody according to the first aspect, and/or an isolated polynucleotide according to the second aspect, and/or a recombinant expression vector according to the third aspect, and/or a host cell according to the fourth aspect, and/or a composition according to the fifth aspect.

In some embodiments, the subject is a mammal, preferably a human subject.

In some embodiments, the disease is a tumor selected from the group consisting of leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder carcinoma, liver cancer, colorectal cancer, breast cancer, ovarian cancer, cervical cancer, endometrial cancer, uterine sarcoma, prostate cancer, bladder cancer, renal cell carcinoma, melanoma.

The present inventors design a completely new anti-PD-L1/anti-PD-1 natural antibody structure-like heterodimeric bispecific antibody, which is a highly stable heterodimeric anti-PD-L1/anti-PD-1 bispecific antibody having characteristics of natural IgGs and having no mismatches heavy chain-light chain. The bispecific antibody can bind simultaneously to two target molecules of PD-L1 and PD-1, block PD-1/PD-L1, PD-1/PD-L2 and CD80/PD-L1 simultaneously, and recruit immune cells to the surface of tumor cells and should exhibit stronger efficacy in tumor treatments.

BRIEF DESCRIPTION OF DRAWINGS

FIG. 9 illustrates the PD-L1-binding activity and PD-1-binding activity of the anti-PD-L1/anti-PD-1 heterodimeric antibody molecule, wherein FIG. 9A and FIG. 9B illustrate the PD-L1-binding activity and the PD-1-binding activity, respectively.

FIG. 10 illustrates that the anti-PD-L1/anti-PD-1 heterodimeric antibody molecule binds simultaneously to SK-BR-3 cells with high expression of PD-L1 and CHO/PD-1 cells with high expression of PD-1, wherein FIG. 10A to FIG. 10D illustrate the bindings of PD-L1 mAb, PD-1 mAb, PD-L1 mAb+PD-1 mAb, and anti-PD-L1/anti-PD-1$_{BJHM}$, respectively.

DETAILED DESCRIPTION

Definitions

Figure 1:
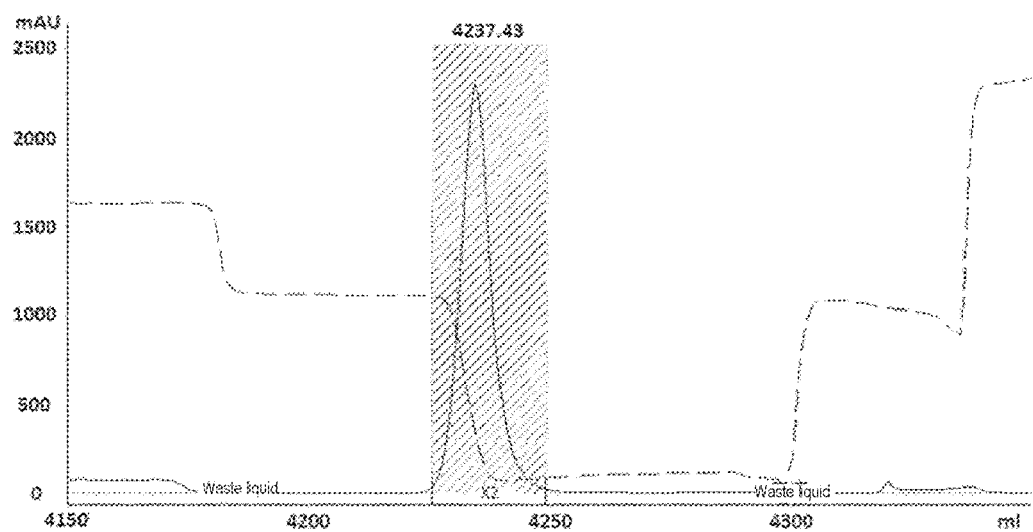
FIG. 1 illustrates the elution peak of a monomer of a heterodimeric antibody molecule.

In a heterodimeric bispecific antibody, "covalent linkage" refers to a covalent bond that links between two Fc chains, or between any one Fc chain and a respective antigen-binding functional region, to form a molecule, wherein the Fc chain comprises a first antigen-binding functional region and a second antigen-binding functional region linked via one or more covalent bonds (e.g., disulfide bonds); the first Fc chain and the second Fc chain are linked respectively to an antigen-binding functional region via a covalent bond (such as an imine bond or an amide bond).

The antigen-binding functional region refers to a region capable of specifically interacting with a target molecule, such as an antigen. Such interaction is highly selective. Generally, a sequence that recognizes one target molecule cannot recognize sequences of other molecules. A representative antigen-binding functional region comprises an antibody variable region, an allosteric antibody variable region, a receptor-binding region, a ligand-binding region, or an enzyme-binding region.

One or more "interchain disulfide bonds" refer to one or more disulfide bonds between the first Fc chain and the second Fc chain, which link the chains to form a heterodimer fragment. In the present invention, one or more disulfide bonds may be formed when the first Fc chain and the second Fc chain, or the first Fc chain and the second Fc chain and the antigen-binding functional regions linked thereto are synthesized in the same cell, or may be formed by in vitro reduction-oxidation process after the first Fc chain and the second Fc chain, or the first Fc chain and the second Fc chain and the antigen-binding functional regions linked thereto are synthesized separately in the different cells.

The first Fc chain and the second Fc chain refer to a combined fragment formed via covalent linkage, wherein the covalent linkage includes a disulfide bond. Each chain comprises at least a portion of an immunoglobulin heavy chain constant region. Moreover, the first chain and the second chain are different in amino acid sequences, including difference in at least one amino acid position. In the first Fc chain and the second Fc chain of the present invention, strong repulsion exists between the same chains, while attraction exists between the different chains. Therefore, the first Fc chain and the second Fc chain, or the first Fc chain and the second Fc chain and the antigen-binding functional regions linked thereto have a tendency to form a heterodimer, when co-expressed in a cell. When the first Fc chain and the second Fc chain, or the first Fc chain and the second Fc chain and the antigen-binding functional regions linked thereto are expressed separately in two host cells, the first Fc chains or the first Fc chain and the antigen-binding functional region linked thereto have no tendency to form a homodimer, and the second Fc chains, or the second Fc chain and the antigen-binding functional region linked thereto have no tendency to form a homodimer. In the present invention, when the first Fc chain and the second Fc chain, or the first Fc chain and the second Fc chain and the antigen-binding functional regions linked thereto are expressed separately in two host cells in the presence of a reducing agent, the proportion of homodimer is less than 50%. That is, the proportion of monomers (an Fc chain or an Fc chain and an antigen-binding functional region linked thereto) is greater than 50%.

An immunoglobulin has a symmetric structure of four polypeptide chains, including two identical heavy chains, which are longer and have a higher relative molecular weight, comprise 450 to 550 amino acid residues and have a relative molecular weight of 55,000 Da to 70,000 Da; two identical light chains (L chains), which are shorter and have a lower relative molecular weight, comprise about 210 amino acid residues and have a relative molecular weight of about 24,000 Da. The sequences of about 110 amino acids near the N-terminus are highly variable in different immunoglobulin heavy and light chains, and are known as variable region (V region). The rest amino acid sequences near the C-terminus are relatively stable, and are known as constant region (C region). In heavy chains, the variable region accounts for about ¼ of the length of the heavy chain, while the constant region accounts for about ¾ of the length of the heavy chain. As for the known five Ig isotypes, i.e., IgG(γ), IgA(α), IgD(δ), IgM(μ) and IgE(ε), there are three constant regions in the H chains of the former three Ig isotypes, i.e., CH1, CH2 and CH3. In the H chains of the latter two isotypes (IgM and IgE), there is one VH region and four constant regions, i.e., CH1 to CH4. The constant region is the framework of immunoglobulin molecules as well as one of regions activating immune responses.

In the present invention, a portion of the constant region includes at least interacting regions of the first Fc chain and the second Fc chain. For IgG, the regions are some amino acids in CH3 regions, including at least GLN347, TYR349, THR350, LEU351, SER354, ARG355, ASP356, GLU357, LYS360, SER364, THR366, LEU368, LYS370, ASN390, LYS392, THR394, PRO395, VAL397, ASP399, SER400, PHE405, TYR407, LYS409, LYS439.

Linking the first Fc chain and the second Fc chain via a covalent bond or a linker respectively to "one antigen-binding functional region" refers to that the first Fc chain and the second Fc chain are linked via a covalent bond or a linker respectively to an antigen-binding fragment of an antibody, or a single-chain antibody capable of recognizing an antigen, or other allosteric antibody fragments capable of recognizing an antigen, or a receptor capable of recognizing a ligand, or a ligand capable of recognizing a receptor. The covalent bond is a kind of chemical bond, wherein two or more atoms share their outer electrons, ideally reaching electronic saturation state, thereby constitute a relatively stable chemical structure called covalent bond. In other words, a covalent bond is the interaction formed between atoms by sharing electron pairs. Atoms of the same element and different elements may both bond via covalent bonds. The covalent bond between the first Fc chain and the second Fc chain of the present invention includes, hut is not limited to, an amide bond formed by a dehydration reaction between an amino groups of one amino acid molecule and a carboxyl group of another amino acid molecule, or an amide bond or imine bond formed from an aldehyde group of ethylene glycol, or polyethylene glycol, or other compounds, or a polymer thereof and an amino group of one amino acid molecule. The linker is a segment of an amino acid sequence, or a compound or a polymer of a compound that can link two polypeptide chains via covalent bonds. The segment of an amino acid sequence includes, but is not limited to, small peptide segments, such as GGGGSGGGGSGGGGS. The first Fc chain or the second Fc chain, and a single-chain antibody capable of recognizing an antigen, or other allosteric antibody fragments capable of recognizing an antigen may be linked via an amide bond.

The context relating to "the first Fc chain and the second Fc chain tend to form heterodimers rather than firming respective homodimers" refers to that for the first Fc chain and the second Fc chain, due to the repulsion existing between the same chains and the attraction existing between the different chains, the first Fc chain and the second Fc chain, or the first Fc chain and the second Fc chain and the antigen-binding functional regions linked thereto have a tendency to form a heterodimer, when co-expressed in a cell. When the first Fc chain and the second Fc chain, or the first Fc chain and the second Fc chain and the antigen-binding functional regions linked thereto are expressed separately in two host cells, the first Fc chains or the first Fc chain and the antigen-binding functional region linked thereto have no tendency to form a homodimer, and the second Fc chains, or the second Fc chain and the antigen-binding functional region linked thereto have no tendency to form a homodimer.

The Kabat index numbering system refers to a method used by Kabat for assigning a number to each amino acid of an antibody sequence, which has become a standard method in the field. The Kabat numbering scheme can be extended to other antibodies beyond his studies. On the basis of conserved amino acids, the target antibody is aligned with one of the consensus sequences identified by Kabat.

"Fc domain" refers to the fragment crystallizable region (Fc), corresponding to CH2 and CH3 domains of Ig, which is the portion for an Ig to interact with an effector molecule or a cell.

IgG, an abbreviation for immunoglobulin G (IgG), is the main antibody component in serum. Human IgG is classified in four subclasses, IgG1, IgG2, IgG3, and IgG4, based on antigenic differences in r chains of IgG molecules.

"Half-antibody" molecule refers to a structure formed by one heavy chain and one light chain of an antibody, wherein the heavy chain and the light chain may be linked via a covalent bond or not. It is a monovalent antibody structure that recognizes an antigen.

"Fab fragment", i.e., the fragment of antigen binding (Fab) is a molecule-recognizing sequence, corresponding to the two arms of an antibody molecule, which is composed of an intact light chain, and the VH and CH1 domains of a heavy chain. "scFv" is a molecule-recognizing sequence, and is a modified antibody fragment obtained by genetic engineering of a light chain variable region and a heavy chain variable region of an antibody "Extracellular region" of a membrane receptor is a molecule-recognizing sequence. The membrane receptor generally includes an extracellular region that locates outside the cell and recognizes and binds to the corresponding antigen or ligand, a transmembrane region that anchors the receptor on the cell surface, and an intracellular region inside the cell, which has intracellular kinase activity or can transmit signaling pathways. "Ligand" of a cell membrane receptor refers to a protein, a small peptide, or a compound that can be recognized and bind to the extracellular region of the membrane receptor. Cytokines are low-molecular weight soluble proteins that are produced by various types of cells induced by immunogens, mitogens, or other stimulants, and have various functions, such as regulation of innate immunity and adaptive immunity, hematopoiesis, cell growth, adult pluripotent stem cells (APSC), and repair of damaged tissues, etc. Cytokines are classed into interleukins, interferons, tumor necrosis factor superfamily, colony stimulating factors, chemokines, growth factors, etc. "Protein expression tag" refers to a segment of amino acid sequence, either a small peptide or a length of amino acids, which is added to the N-terminus or C-terminus of a target protein. Addition of tags may be advantageous to correct folding of proteins, isolation and purification of proteins, and reduction of intracellular degradation of proteins. Commonly used tags include, but are not limited to, HA, SUMO, His, GST, GFP, and Flag.

There is no limitation to the antibodies applicable to a heterodimeric bispecific antibody of the present invention. Preferably, any antibodies known in the art for the treatment and/or prevention of diseases can be used in the present invention.

The heterodimeric bispecific antibody of the present invention may have one or more substitutions, deletions, additions, and/or insertions. For example, some amino acids can substitute for the other amino acids in the protein structure without significant loss of the capability in binding to other polypeptides (such as antigens) or cells. Since the biological functional activity of a protein is determined by the binding ability and properties of the protein, the protein sequence can be subjected to substitution of some amino acid sequences without significant loss of its biological effector activity.

In many cases, polypeptide variants comprise one or more conservative substitutions. "Conservative substitution" refers to the substitution of an amino acid with other amino acids having similar properties, such that a person skilled in the art of peptide chemistry would expect the secondary structure and hydrophilic properties of the polypeptide to be substantially unchanged.

Amino acid substitutions are generally based on the relative similarity of the side-chain substituents of amino acids, such as their hydrophobicity, hydrophilicity, charge, size, etc. Considering the various characteristics described above, the exemplary substitutions are well known to a person skilled in the art, and include: arginine and lysine; glutamic acid and aspartic acid; serine and threonine; glutamine and asparagine; and valine, leucine, and isoleucine.

The term "identity" used in the present invention has the meaning commonly known in the art, and refers to the percentage of identical residues between a polynucleotide or polypeptide sequence variant and a non-variant sequence, upon aligning the sequences and introducing gaps (if necessary, to achieve the maximum % homology). The rules and criteria for determining the identity between different sequences are also known to a person skilled in the art. In the present invention, when the definition of identity is satisfied, it is also required that the obtained variant sequence has the biological activity possessed by the parent sequence. Methods and means for screening variant sequences with the above activity are well known to a person skilled in the art. From the teachings disclosed herein, one skilled in the art would readily achieve such variant sequences. In a specific embodiment, the polynucleotide and polypeptide variants have at least about 70%, at least about 75%, at least about 80%, at least about 90%, at least about 95%, at least about 98%, or at least about 99%, or at least about 99.1%, 99.2%, 99.3%, 99.4%, 99.5%, 99.6%, 99.7%, 99.8% or 99.9% polynucleotide or polypeptide identity with the polynucleotide or polypeptide described herein. Due to redundancy of the genetic codes, there are variants encoding the same amino acid sequence as these sequences.

In another embodiment of the present invention, a polynucleotide composition capable of hybridizing with the polynucleotide sequence provided by the present invention, or a fragment thereof, or a complementary sequence thereof under moderately to highly stringent conditions is provided. Hybridization techniques are well known in the field of molecular biology. For illustrative purposes, suitable moderately stringent conditions for testing hybridization of the polynucleotide of the present invention with other polynucleotides include pre-washing with a solution of 5×SSC, 0.5% SDS, 1.0 mM EDTA (pH 8.0); hybridizing under the conditions of 5×SSC at 50° C.-60° C. overnight; and washing at 65° C. with 2×, 0.5× and 0.2×SSCs containing 0.1% SDS twice for 20 minutes. A person skilled in the art understands that the stringency of hybridization may be readily manipulated, for example, by varying the salt content of the hybridization solution and/or the hybridization temperature. For example, in another embodiment, suitable highly stringent hybridization conditions include the conditions described above, except for increasing the hybridization temperature, for example, to 60-65° C. or 65-70° C.

The host cell of the present invention may be any cell used for heterologous gene expression, including but not limited to E. coli, yeast, insect cells, plant cells, and mammalian cells.

The vector of the present invention includes a vector that can replicate in any type of cells or organisms, including but not limited to, for example, plasmids, is bacteriophages, cosmids, and minichromosomes. In some embodiments, the vector comprising the polynucleotide of the present invention is a vector suitable for propagation or replication of a polynucleotide, or a vector suitable for expression of the polypeptide of the present invention. Such a vector is known in the art and is commercially available.

"Vectors" include shuttle vectors and expression vectors. Generally, a plasmid construct also includes an origin of replication (e.g., CoE1 origin of replication) and a selectable marker (e.g., ampicillin or tetracycline resistance) used respectively for plasmid replication and selection in bacteria. "Expression vector" refers to a vector comprising a control sequence or a regulatory element required for expressing the antibody of the present invention, including antibody fragments, in bacteria or eukaryotic cells.

The vector of the present invention may be any vector used for heterologous gene expression, including but not limited to, a plasmid vector, wherein the plasmid vector comprises at least an origin of replication, a promoter, a gene of interest, a multiple cloning site and a selective marker gene. Preferably, the vector of the present invention includes, but is not limited to, a plasmid vector obtained by modification based on pcDNA, such as X0GC vector.

The subject of the present invention includes poultry, reptiles, mammals, etc. Preferably, the mammals include rodents and primates. Preferably, the primates include humans.

The scope of the diseases involved in the present invention includes, but is not limited to, tumors. Preferably, the tumors include: leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder carcinoma, liver cancer, colorectal cancer, breast cancer, ovarian cancer, cervical cancer, endometrial cancer, uterine sarcoma, prostate cancer, bladder cancer, renal cell carcinoma, melanoma.

A pharmaceutically acceptable carrier refers to a pharmaceutical carrier which is commonly used in the pharmaceutical field, for example, diluents, excipients, water, etc.; fillers such as starch, sucrose, lactose, microcrystalline cellulose, etc.; binders such as cellulose derivatives, alginates, gelatin and polyvinyl pyrrolidone; wetting agents such as glycerin; disintegrating agents such as sodium carboxymethyl starch, hydroxypropyl cellulose, crosslinked carboxymethyl cellulose, agar, calcium carbonate, sodium bicarbonate; absorption enhancers such as quaternary ammonium compounds; surfactants such as hexadecanol, sodium laurel sulfate; adsorption carriers such as kaolinite, bentonite; lubricants such as talc, calcium stearate and magnesium stearate, micronized silica gel and polyethylene glycol, etc. In addition, other adjuvants such as a flavoring agent and a sweetening agent may be added to the composition.

The present invention will be further explained hereinafter with reference to the non-limiting examples as follows.

It is commonly known by a person skilled in the art that various modifications may be made to the present invention without departing from the spirit of the present invention. Such modifications also fall within the scope of the present invention.

The following experimental methods are all common methods unless otherwise specified. The experimental materials employed can be readily obtained from commercial companies unless otherwise specified. The antibodies used in the following Examples of the present invention are all standard antibodies which are commercially obtained.

EXAMPLE 1

Vector Construction of a Heterodimeric Antibody Molecule

X0GC expression vectors respectively comprising the heavy chain and light chain of an anti-PD-L1 antibody were constructed, wherein the sequences of the antibody variable regions were from https://www.drugbank.ca/drugs/DB11595. The heavy chain constant region was derived from human IgG1. The nucleotide sequence of the light chain variable region is shown as SEQ ID NO: 1, the amino acid sequence thereof is shown as SEQ ID NO: 2; the nucleotide sequence of the light chain constant region is shown as SEQ ID NO: 3, the amino acid sequence thereof is shown as SEQ ID NO: 4; the nucleotide sequence of the heavy chain variable region is shown as SEQ ID NO: 5, the amino acid sequence thereof is shown as SEQ ID NO: 6; the nucleotide sequence of the heavy chain constant region is shown as SEQ ID NO: 7, the amino acid sequence thereof is shown as SEQ ID NO: 8. The light chain variable region and the light chain constant region, the heavy chain variable region and the heavy chain constant region were amplified by PCR method, respectively. Phusion High-Fidelity DNA Polymerase (F-530L; by NEB, Inc.) was used in all PCR reactions of the present application. PCR primers were conventionally designed according to the principle of complementary base pairing, and the requirement of enzyme digestion sites. All the reaction systems were: 8.9 μl of H$_2$O, 4 μl of 5× Phusion High-Fidelity DNA Polymerase buffer, 4 μl of 1 nM dNTP, 1 μl of upstream primer, 1 μl of downstream primer, 0.1 μl of Phusion High-Fidelity DNA Polymerase, and 1 μl of the template. The PCR products of the variable regions and the constant regions were subjected to 1.5% agarose gel electrophoresis and the corresponding fragments were recovered using a DNA recovery kit (Promega, A9282, the same below). A further PCR was performed with the recovered variable region fragment and constant region fragment as templates, using an upstream primer of the variable region and a downstream primer of the constant region. Then the corresponding fragments were recovered to obtain a full-length fragment of the light chain or heavy chain. The X0GC vector and the full-length fragments were digested with EcoRI (NEB; Catalog No. R3101L) and HindIII (NEB; Catalog No. R3104L). The enzyme digestion reaction system was: 2 μl of 10× buffer 3, 0.5 μl each of EcoRI and HindIII, 3 μl of the full-length fragments recovered from the gel, and 14.5 μl of H$_2$O. The enzyme digestion system was allowed to react at 37° C. for 3 hours. The enzyme digestion products were ligated with T4 DNA ligase (NEB; Catalog No. M0202V) (the same hereinafter). The reaction system was: 2 μl of 10× ligase buffer, 0.5 μl of ligase, 3 μl of the full-length fragments recovered from the gel, 3 μl of the X0GC vector recovered from the gel, and 11.5 μl of H$_2$O. The ligation was carried out at room temperature for 12 hours. The ligated products were transformed into E. coli DH5α competent cells (Tiangen, CB104, the same hereinafter), to obtain the respective X0GC expression vectors of the antibody heavy chain and light chain, for expressing the antibody heavy chain and light chain in eukaryotic cells, respectively.

The X0GC expression vectors of the heavy chain and the light chain of the anti-PD-1 (Pem) antibody were constructed, respectively, wherein the sequences of the antibody variable regions were from http://www.imgt.org/3Dstructure-DB/cgi/details.cgi?pdbcode=9798. The nucleotide sequence of the light chain variable region is shown as SEQ ID NO: 9, the amino acid sequence thereof is shown as SEQ ID NO: 10; the nucleotide sequence of the light chain constant region is shown as SEQ ID NO: 3, the amino acid sequence thereof is shown as SEQ ID NO: 4; the nucleotide sequence of the heavy chain variable region is shown as SEQ ID NO: 11, the amino acid sequence thereof is shown as SEQ ID NO: 12; the nucleotide sequence of the heavy chain constant region is shown as SEQ ID NO: 13, the amino acid sequence thereof is shown as SEQ ID NO: 14. The respective X0GC expression vectors of the antibody heavy chain and light chain were obtained for expressing the antibody heavy chain and light chain in eukaryotic cells, respectively.

The X0GC expression vectors of the heavy chain and light chain of the anti-PD-1 antibody (BJHM) were also constructed in present invention. The nucleotide sequence of the light chain variable region is shown as SEQ ID NO: 15, the amino acid sequence thereof is shown as SEQ ID NO: 16; the nucleotide sequence of the light chain constant region is shown as SEQ ID NO: 3, the amino acid sequence thereof is shown as SEQ ID NO: 4; the nucleotide sequence of the heavy chain variable region is shown as SEQ ID NO: 17, the amino acid sequence thereof is shown as SEQ ID NO: 18; the nucleotide sequence of the heavy chain constant region is shown as SEQ ID NO: 13, the amino acid sequence thereof is shown as SEQ ID NO: 14. The respective X0GC expression vectors of the antibody heavy chain and light chain were obtained for expressing the antibody heavy chain and light chain in eukaryotic cells, respectively.

EXAMPLE 2

Expression of the Heterodimeric Antibody Molecule

The respective expression vectors of the antibody heavy chain and the light chain were co-transfected into 293F cell lines (FreeStyle™ 293-F Cells, Cat. No. R79007, Invitrogen). One day before transfection, the cells were inoculated. On the day of transfection, the cells were collected by centrifugation, and then re-suspended in fresh FreeStyle™ 293 expression medium (Cat. No. 12338001; Gibco) at a cell density of 200×10$^5$ cell/mL. Plasmids were added according to the transfection volume to a final concentration of 36.67 ug/mL, and mixed gently. Next, linear PEI (polyethyleneimine, linear, M.W. 25000, Cat. No, 43896, Alfa Aesar) was added to a final concentration of 55 ug/mL, and mixed gently. Thereafter, the mixture was placed in a cell incubator, and incubated in a shaker at 120 rpm, 37° C. for 1 hour. Then, a fresh medium in a volume of 19 times of the transfection volume was added. Incubation continued in the shaker at 120 rpm, 37° C. The supernatants of the cell culture transfected for 5-6 days were collected by centrifugation.

The expression amount was determined by ELISA method. Before purification by applying a chromatographic column, the precipitates were removed by filtration through a 0.2 μm filter membrane. This step was performed at 4° C.

EXAMPLE 3

Purification of the Heterodimeric Antibody Molecule Expression Product

Purification was performed at 4° C. using AKTA Explorer 100 Protein Purification System (GE Healthcare) and rProtein A Sepharose Fast Flow affinity chromatographic column (16 mm I.D., 22 ml, GE Healthcare). First, the chromatographic column was equilibrated with mobile phase A (20 mM sodium phosphate buffer, 150 mM sodium chloride, pH 7.4). After the baseline was stabilized, the cell supernatant treated as above was loaded at a flow rate of 5 ml/min. After the loading process, the mobile phase A was used for equilibration. Thereafter, 5 column volumes of mobile phase B1 (mobile phase A plus 0.5 M arginine) were used for washing the column; and 5 column volumes of mobile phase B2 (100 mM citric acid, pH 3.0) were used for eluting to collect an elution peak, i.e., the peak of the protein of interest. The flow rate in all the above elution steps was 5 ml/min. A chromatogram of the elution peak of the anti-PD-L1 expression product is illustrated in FIG. 1. The elution peak of the anti-PD-1 expression product is similar thereto (the result is not included). The indicated elution peak (grey area as shown) was collected and the pH was adjusted to pH 5.0 by dropwise addition of 1 M sodium acetate solution.

Figure 2:
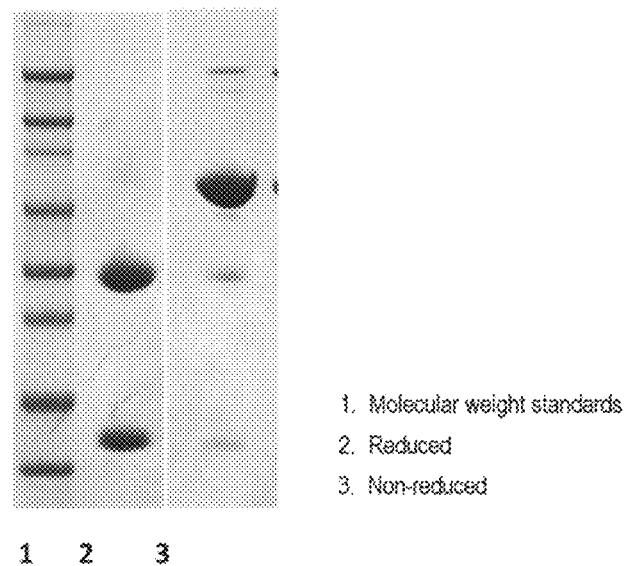
FIG. 2 illustrates the SDS-PAGE analysis of a monomer of a heterodimeric antibody molecule.

The purified products were analyzed by SDS-PAGE method, and the results were shown in FIG. 2.

EXAMPLE 4

Figure 3:
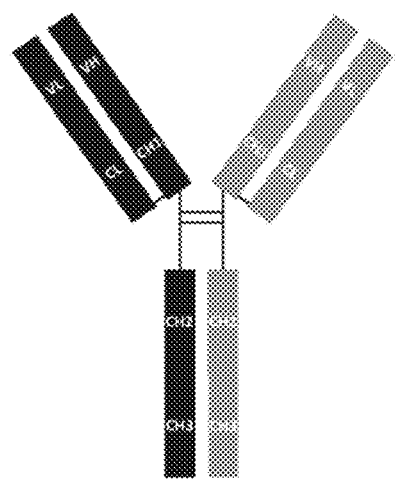
FIG. 3 illustrates the structure of an anti-PD-L1/anti-PD-1 heterodimeric antibody molecule.

Preparation and Purification of the Anti-PD-L1/Anti-PD-1 Heterodimeric Antibody Molecule The structure of the anti-PD-L1/anti-PD-1 heterodimeric antibody molecule is illustrated in FIG. 3.

Figure 4:
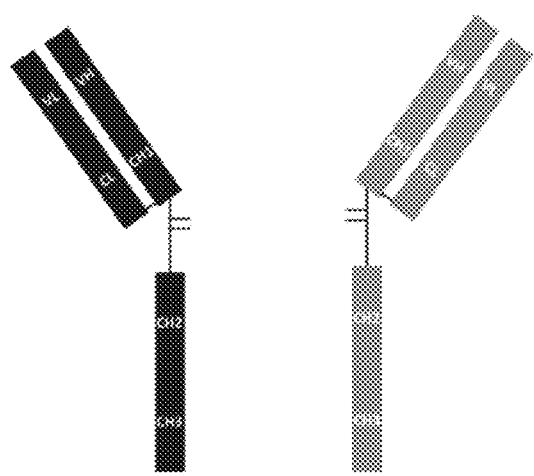
FIG. 4 illustrates the schematic structures of half-antibody molecules of one heavy chain and one light chain.

The half-antibody molecule of the antibody obtained in the above method of rProtein A Sepharose Fast Flow (16 mm I.D., 22 ml, GE Healthcare) was subjected to in vitro re-assembly to obtain a heterodimer. The protein solution purified and collected as the above was firstly concentrated by ultrafiltration through an ultrafiltration concentrating tube (nominal cut-off molecular weight of 10 kDa), and then the solution was displaced by phosphate buffer saline (PBS) (pH=7.4). The obtained molecular solutions of the half-antibody molecules of the anti-PD-L1 and anti-PD-1 antibodies were adjusted to 1 mg/ml by adding PBS respectively. 1 M DTT was added at 1/200 times of the final volume, such that the final concentration of DTT was 5 mM, respectively. Reduction was carried out at 4° C. (3 to 8 hours) to break disulfide bonds. The disulfide bonds in the hinge region of homodimeric antibody molecules contained at a small amount in the anti-PD-1 half antibody molecules were also broken, thereby forming half-antibody molecules comprising one heavy chain and one light chain, as the structure illustrated in FIG. 4. The reduced sample was analyzed with SEC-HPLC. The proportion of the half antibody molecule was more than 90%.

Figure 5:
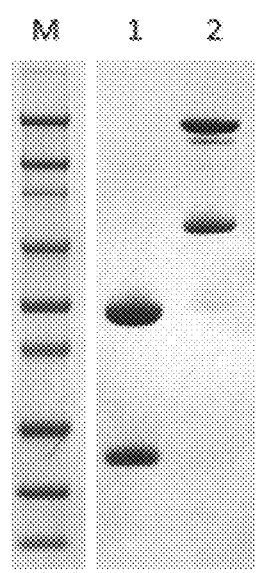
FIG. 5 illustrates the results of SDS-PAGE analysis of an oxidized product of the half-antibody molecules of anti-PD-L1 and anti-PD-1 antibodies.

Thereafter, the reduced anti-PD-L1 and anti-PD-1 half-antibody molecules were mixed in an equimolar ratio, and subjected to re-assembly reaction at 4° C. for 24 hours. During re-assembly, a heterodimeric bispecific antibody comprising both the anti-PD-L1 and anti-PD-1 half-antibody molecules was formed from the anti-PD-L1 and anti-PD-1 half-antibody molecules via the non-covalent interaction between CH2/CH3. Then, the protein solution was concentrated by ultrafiltration through an ultrafiltration concentrating tube (nominal cut-off molecular weight of 10 kDa). The solution was displaced by phosphate buffer saline (PBS) (pH=7.4) to stop reduction. Oxidation was carried out in air or with an oxidizing agent to allow re-formation of disulfide bonds of the heterodimeric bispecific antibody. The oxidation conditions were as follows: addition of 100 mM L-dehydroascorbic acid as the oxidizing agent; the final concentration of the protein was 1 mg/ml and the final concentration of the oxidizing agent was 1 mM; oxidation reaction was performed at 4° C. for 24 hours. A sample obtained by the above-described oxidation reaction was subjected to SDS-PAGE analysis. The results are shown in FIG. 5.

Figure 6:
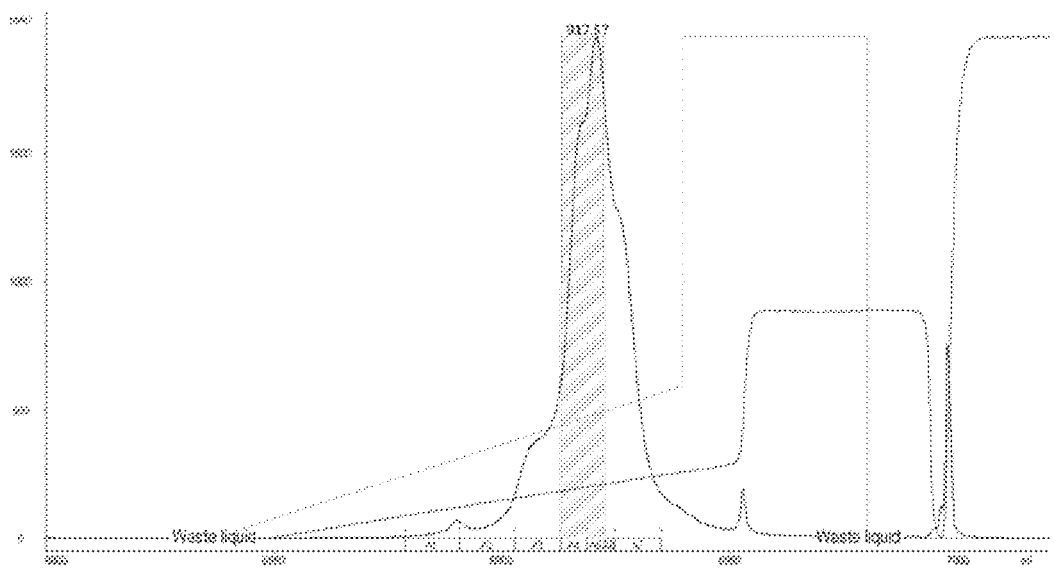
FIG. 6 illustrates the elution peak of the anti-PD-L1/anti-PD-1 heterodimeric antibody molecule.
Figure 7:
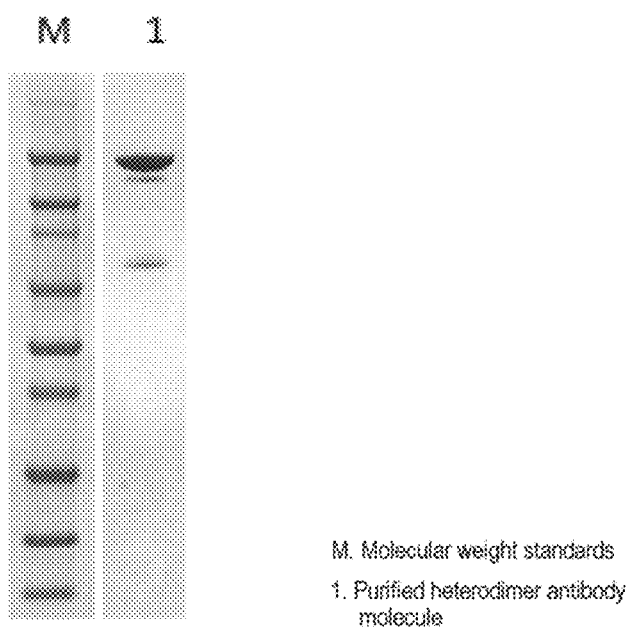
FIG. 7 illustrates the results of SDS-PAGE analysis of the anti-PD-L1/anti-PD-1 heterodimeric antibody molecule.
Figure 8:
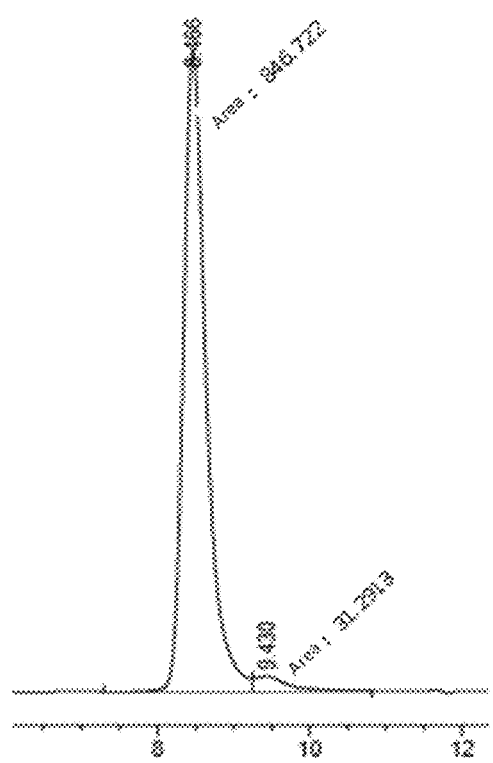
FIG. 8 illustrates the results of SEC analysis of the anti-PD-L1/anti-PD-1 heterodimeric antibody molecule.

The heterodimer molecule obtained by the above reduction-oxidation of the above anti-PD-L1 and anti-PD-1 half-antibody molecules was concentrated by ultrafiltration through an ultrafiltration concentrating tube (nominal cut-off molecular weight of 10 kDa). The solution was displaced by 10 mM sodium phosphate buffer (pH=5.8). Purification was performed at 4° C. using AKTA Explorer 100 Protein Purification System (GE Healthcare) and ion chromatography column Source 15S (16 mm I.D., 17 ml, GE Healthcare). First, the chromatographic column was equilibrated with mobile phase A (10 mM sodium phosphate buffer, pH 7.0). After the baseline was stabilized, the protein solution treated as above was loaded at a flow rate of 3 ml/min. After the loading process, the mobile phase A was used fir equilibration. Thereafter, the column was eluted with 20 column volumes at a gradient of A (10 mM sodium phosphate, pH 5.8) to B (10 mM sodium phosphate, pH 5.8) (0% B-100% B, 170 min, flow rate 2 ml/min). The min eluting peak as indicated was collected (shown in FIG. 6), and the collected protein solution was concentrated by ultrafiltration through an ultrafiltration concentrating tube (nominal cut-off molecular weight of 10 kDa). The solution was displaced by phosphate buffer saline (PBS, pH=7.4), sterilized by filtration, and stored at 4° C. The purified product was analyzed by SDS-PAGE method. Results are shown in FIG. 7. Upon purity analysis by SEC-HPLC, the purity was 96.44%, as the results shown in FIG. 8.

EXAMPLE 5

In Vitro Target-Binding Activity of the Anti-PD-L1/Anti-PD-1 Heterodimeric Antibody Molecule The binding ability of the PD-L1/PD-1 heterodimeric antibody to a single antigen was determined by enzyme-linked immunosorbent assay (ELISA).

Detailed process of the assay is as follows: Recombinant human PD-L1 (Beijing Sino Biological Inc., Cat. No. 10377-H08H) or human PD-1 (Beijing Sino Biological Inc., Cat. No. 10377-H08H) was coated on a 96-well highly-adsorptive ELISA plate using carbonate buffer at pH 9.6, at a coating concentration of 1 μg/mL in a coating amount of 100 μL per well. The coating was performed at 4° C. overnight. The plate was washed with PBST for five times. Then the plate was blocked with 300 μL/well of PBST containing 1% BSA, and incubated for 1 hour at 25° C., and then washed with PBST for five times. The samples of the heterodimeric antibody and the control, which were serially diluted with PBST containing 1% BSA, were added at 100 μL/well, and incubated at 25° C. for 1 hour. The plate was washed with PBST for five times. Then, horseradish peroxidase-labeled anti-human IgG antibody (Chemicon, Cat. No. AP309P) diluted at 1:2000 with PBST containing 1% BSA was added at 100 μL/well, and incubated at 25° C. for 1 hour. The plate was washed with PBST for five times. A colorimetric substrate TMB was added at 100 μL/well and developed for 10 minutes at room temperature. Color development was terminated by adding 1 M $H_2SO_4$ at 100 μL/well. The absorbance at 450 nm was read on a microplate reader.

Figure 9:
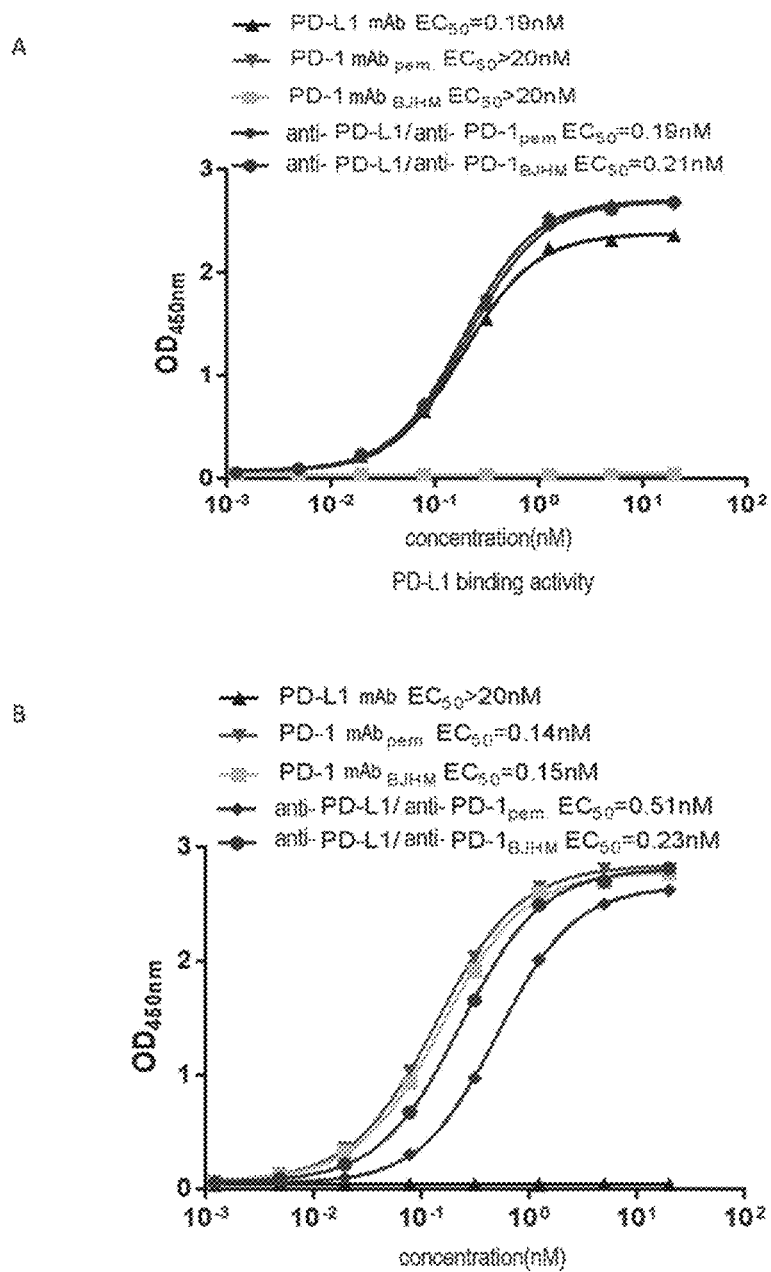

According to the results shown in FIG. 9, both anti-PD-L1/anti-PD-$1_{pem}$ and anti-PD-L1/anti-PD-$1_{BJHM}$ have high affinity for PD-L1 and PD-1; the antigen affinity activity of the bivalent monoclonal antibody was well retained. In the above, anti-PD-L1/anti-PD-$1_{BJHM}$ has higher PD-1 affinity than anti-PD-L1/anti-PD-$1_{pem}$.

EXAMPLE 6

The Activity of the Anti-PD-L1/Anti-PD-1 Heterodimeric Antibody Molecule of Inducing Cell Association by Simultaneously Binding to Dual Targets The activity of the PD-L1/PD-1 heterodimeric antibody of inducing cell association by simultaneously binding to dual targets was determined on HCC827 cells expressing PD-L1 and CHO/PD-1 cells with high PD-1 expression (GenScript, Cat. No. M00529) by fluorescence activated cell sorting (FACS).

CHO/PD-1 cells were stained according to the instructions of PKH26 kit (Sigma, Cat. No. SLBH4568V). Briefly, CHO/PD-1 cells were collected, washed once with serum-free medium, and suspended at $2 \times 10^7$/mL with Diluent C in the PKH26 kit. The PKH26 dye was diluted to 4 μM with Diluent C, and mixed with the cell suspension at 1:1 ratio. The mixed suspension having cell density of $1 \times 10^7$/mL and PKH26 concentration of 2 μM was incubated for 1 minute at room temperature, and then incubated with an equal volume of FBS for 1 minute to terminate the staining. The suspension was centrifuged at 400 g for 10 minutes, washed twice with a complete medium, and re-suspended in the complete medium for further use. HCC827 cells were stained according to instructions of CFSE kit (Life technology, Cat. No. C34554). Briefly, the CFSE was diluted with PBS to working concentration of 0.5 μM and pre-heated at 37° C. The HCC827 cells were collected by centrifugation at 1000 rpm for 5 minutes, and then suspended with the pre-heated CFSE working solution and incubated at 37° C. for 15 minutes. The cells were collected by centrifugation at 1000 rpm for 5 minutes, re-suspended in the complete medium, and incubated for 30 minutes. Then the cells were washed once with the complete medium and then re-suspended in the complete medium for further use.

The above stained cells were collected by centrifugation and washed once with cold PBS containing 2% FBS. The cells were re-suspended in cold PBS containing 2% FBS at a cell density of $5 \times 10^6$/mL. HCC827 and CHO/PD-1 cells were mixed at 1:1 ratio. 100 μL of the cell mixture was taken into each flow tube (i.e., $2.5 \times 10^5$ HCC827 and $2.5 \times 10^5$ CHO/PD-1), and then 100 μL of the heterodimeric antibody sample diluted in cold PBS containing 2% FBS, the control, or isotype control (human immunoglobulin, Jiangxi Boya Biopharmaceutical Co., Ltd., National Drug Approval No. S19993012) were added. The flow tubes were incubated on ice for 30 minutes, washed twice with PBS containing 2% FBS and then re-suspended in 500 μL cold PBS. The cell suspension was detected and analyzed with a flow cytometry.

Figure 10:
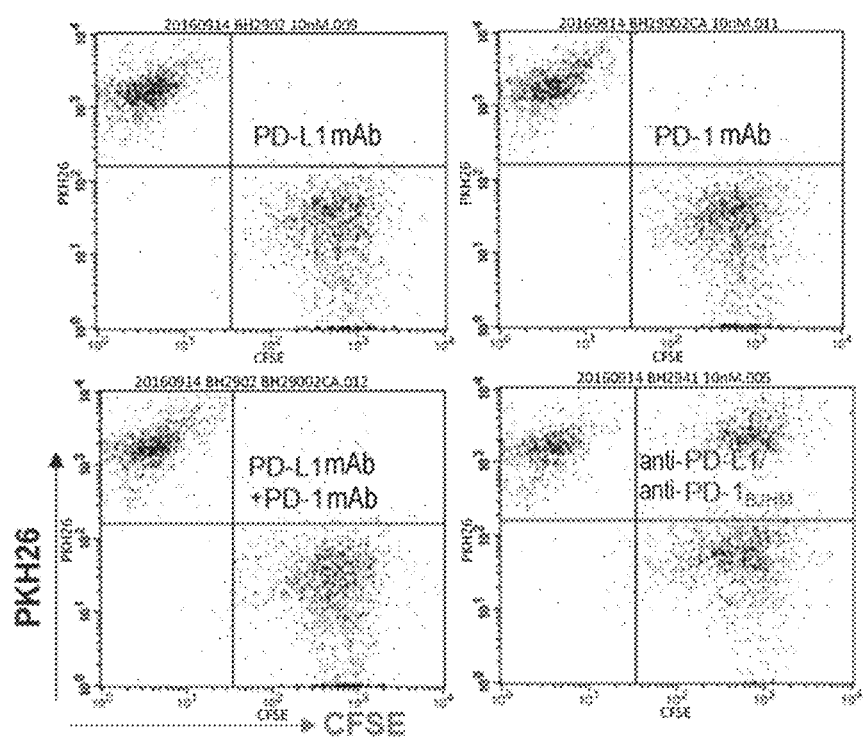

The results are shown in Table 1 and FIG. 10. By simultaneous binding to HCC827 cells expressing PD-L1 and CHO/PD-1 cells with high PD-1 expression with the heterodimeric antibody, the PD-L1/PD-1 heterodimeric antibody can induce close association between HCC827 and CHO/PD-1 cells, which is the basis for mediating tumor cell killing by T cells.

TABLE 1

| Percentage of cells induced in close association | |
|---|---|
| Samples | % associated cells |
| Isotype control | 2.23 |
| PD-L1 mAb (10 nM) | 1.96 |
| PD-1 mAb $_{pem}$ (10 nM) | 2.45 |
| PD-1 mAb $_{BJHM}$ (10 nM) | 2.21 |
| PD-L1mAb(10 nM) + PD-1mAb(10 nM) | 2.38 |
| Anti-PD-L1/Anti-PD-$1_{pem}$(10 nM) | 26.22 |
| Anti-PD-L1/Anti-PD-$1_{BJHM}$ (0.1 nM) | 4.69 |
| Anti-PD-L1/Anti-PD-$1_{BJHM}$ (1 nM) | 25.05 |
| Anti-PD-L1/Anti-PD-$1_{BJHM}$ (10 nM) | 26.01 |

EXAMPLE 7

T Cell Regulatory Activity of the Anti-PD-L1/Anti-PD-1 Heterodimeric Antibody Molecule The regulatory activity of the PD-L1/PD-1 heterodimeric antibody on T cell immune response was determined by mixed lymphocyte reaction (MLR).

Acquisition of human dendritic cells (DC): Human PBMC cells (Lanza, Cat. No. CC-2702) were resuscitated and collected. The human PBMC cells were re-suspended in serum-free RPMI 1640 medium at cell density of $5 \times 10^6$/mL, innoculated in a cell culture flask, and incubated in $CO_2$ incubator at 37° C. for 90 minutes. After disposal of culture supernatant and suspending cells, the adherent cells were cultured in the complete medium (RPMI 1640 containing 10% FBS) added with 100 ng/ml GM-CSF (Beijing Sino Biological Inc., Cat. No. 10015-HNAH) and 100 ng/ml IL-4 (Beijing Sino Biological Inc., Cat. No. 11846-HNAE). After incubation for 3 days, the medium was replaced, and the cells were incubated for another 3 days. Then the culture medium was replaced with the complete medium (RPMI 1640 containing 10% FBS) containing 100 ng/ml GM-CSF, 100 ng/ml IL-4 and 20 ng/ml TNF-α, and the cells were incubated for 1 day to obtain DC cells.

Acquisition of human T cells: Human PBMC cells were resuscitated and collected, ensuing that this PBMC cells and the PBMC for inducing DC cells came from different individuals. The human T cells were separated according to the instructions of the Pan T Cell Separation kit (Miltenyi Biotech, Cat. No. 5150414820). Briefly, the PBMC was washed with PBS once, and re-suspended at $10^7$ cells (the amounts were all calculated in $10^7$ cells hereinafter) per 40 μL separation buffer (PBS containing 2 mM EDTA, 0.5% BSA, pH=7.2). 10 μL Pan T cell Biotin Antibody Cocktail was added and incubated at 4° C. for 5 minutes. After that, 30 μL separation buffer and 20 μL Pan T cell MicroBead Cocktail were added and incubated at 4° C. for 10 minutes. T cells were obtained through the MACS separation column.

The collected human DC cells and human T cells were re-suspended in the complete medium (RPMI 1640 containing 10% FBS) and inoculated on a 96-well plate at 1×10⁴/well and 1×10⁵/well, respectively, and cultured in mixture. The samples of the PD-L1/PD-1 heterodimeric antibody serially diluted in a complete medium and the control were added. The culture plate was placed in a $CO_2$ incubator for incubation at 37° C. for 5 days. Upon completion of incubation, the supernatant in the wells was taken and the cytokines IL-2 (Ray Biotech, Cat. No. ELH-IL2) and IFN-γ (Ray Biotech, Cat. No. ELH-IFNg) were detected according to the kit manuals.

Figure 11:
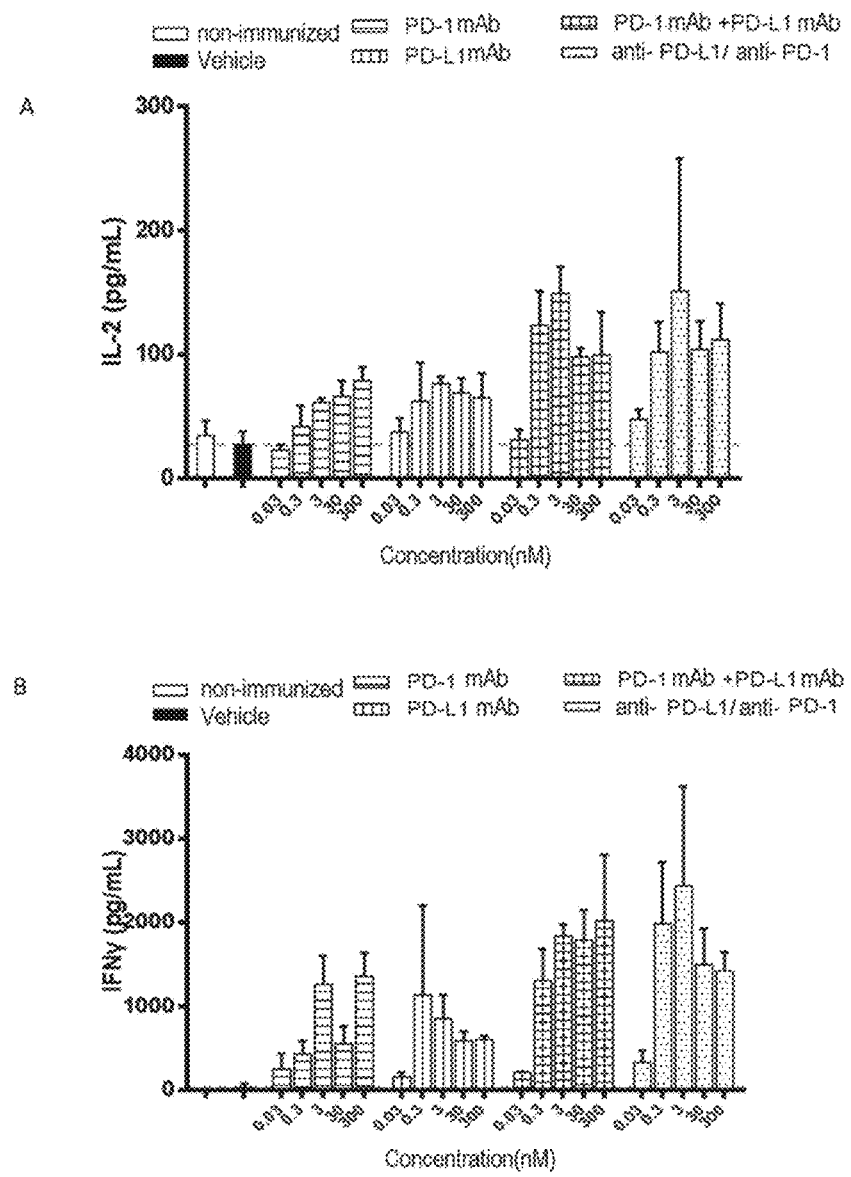
FIG. 11 illustrates that the anti-PD-L1/anti-PD-1 heterodimeric antibody molecule promotes the secretion of cytokines IL-2 and IFN-gamma.

As shown in FIG. 11, the human T cells stimulated by allogeneic DC cells can activate and secrete IL-2 and IFN-γ. The addition of the PD-L1 antibody or the PD-1 antibody can enhance the activation of T cells and promote the secretion of cytokines. The PD-L1/PD-1 heterodimeric antibody has stronger T cell regulatory activity than the monoclonal antibody, and promotes the secretion of cytokines IL-2 and IFN-γ more significantly.

EXAMPLE 8

In Vitro Killing Activity of the Anti-PD-L1/Anti-PD-1 Heterodimeric Antibody Molecule on Tumor Cells The HCC827 tumor cells were collected. The HCC827 cells were re-suspended in the complete medium (RPMI 1640 containing 10% FBS) at cell density of 5×10⁴/mL, and inoculated on a 96-well plate at 100 μL per well (5×10³ cells in each well). The plate was incubated for 3-4 hours in a $CO_2$ incubator at 37° C. for 3-4 hours. The human PBMC cells (Lonza, Cat. No. CC-2702) were resuscitated and collected. The PBMC was re-suspended in the complete medium (RPMI 1640 containing 10% FBS) at cell density of 2×10⁶/mL, and added into the 96-well plate at 50 μL/well (1×10⁵ cells per well), so that the ratio of effector cells to target cells was 20:1. Trop-2/CD3 heterodimeric antibody (Beijing Hanmei Pharm.) was added at the final concentration of 1 nM. The samples of the PD-L1/PD-1 heterodimeric antibody serially diluted in the complete medium and the control were added. The total volume of the liquids in each well was 200 μL. The incubation plate was placed in a $CO_2$ incubator for incubation at 37° C. for 3 days.

At the end of incubation, the culture supernatant and suspending PBMC cells were discarded. The HCC827 cells were washed with PBS twice to remove the residual PBMC. Finally, 100 μL complete medium and 20 μL MTS color developer (Promega, Cat. No. G358B) were added and incubated for 2-3 hours. The absorption at 490 nm was detected with a microplate reader.

Figure 12:
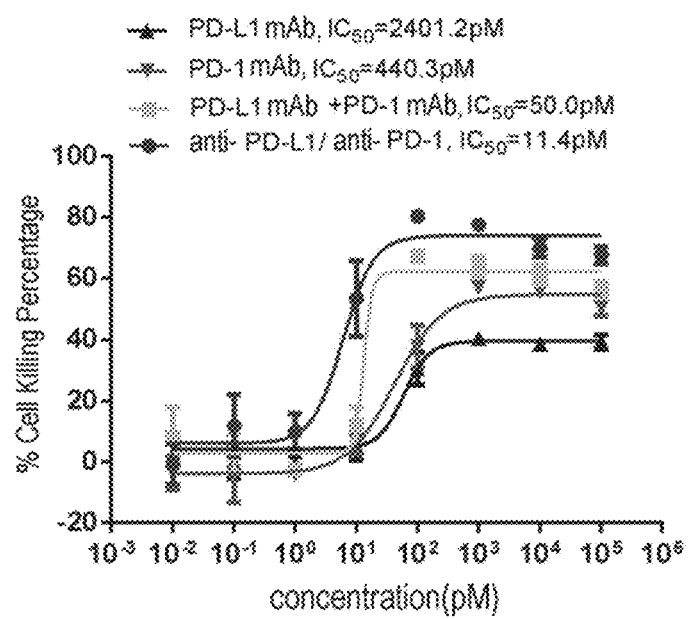
FIG. 12 illustrates the in vitro killing activity of PD-L1/PD-1 heterodimeric antibody molecule on tumor cells.

As shown in FIG. 12, when the Trop-2/CD3 heterodimeric antibody initiated cell killing by PBMC on HCC827 tumor cells, the PD-L1 antibody or PD-1 antibody can enhance PBMC's killing effect on tumor cells in a concentration-dependent manner, while the PD-L1/PD-1 heterodimeric antibody has stronger killing activity on tumor cells than the monoclonal antibody and combinations of monoclonal antibodies.

EXAMPLE 9

Anti-Tumor Efficacy of the Anti-PD-L1/Anti-PD-1 Heterodimeric Antibody Molecule in an Xenotransplantation Tumor Model Female NPG (NOD-Prkdc$^{scid}$ Il2rg$^{null}$) mice aged 6-8 weeks purchased from Beijing Vitalstar Biotechnology Co. Ltd. were used as the experimental materials. After environmental adaptation for one week, 5×10⁶ HCC827 human lung cancer cells were subcutaneously inoculated into the right back of each mouse. When the tumor volume grew to about 100 mm³, the mice were grouped according to the tumor volume, six tumor-bearing mice in each group. The animals were respectively given a vehicle (PBS), 70 nmol/kg of PD-L1 monoclonal antibody, 70 nmol/kg of PD-1 monoclonal antibody, a pharmaceutical composition of 70 nmol/kg of PD-L1 monoclonal antibody+70 nmol/kg of PD-L1 monoclonal antibody, and 70 nmol/kg of anti-PD-1 heterodimer, by intraperitoneal injections twice per week, for two weeks. Starting from the date of administration, the tumor volumes were measured three times a week. The long diameter a and short diameter b were measured, and the tumor volumes was calculated according to the formula of tumor volume $(mm^3)=(a \times b^2)/2$.

Figure 13:
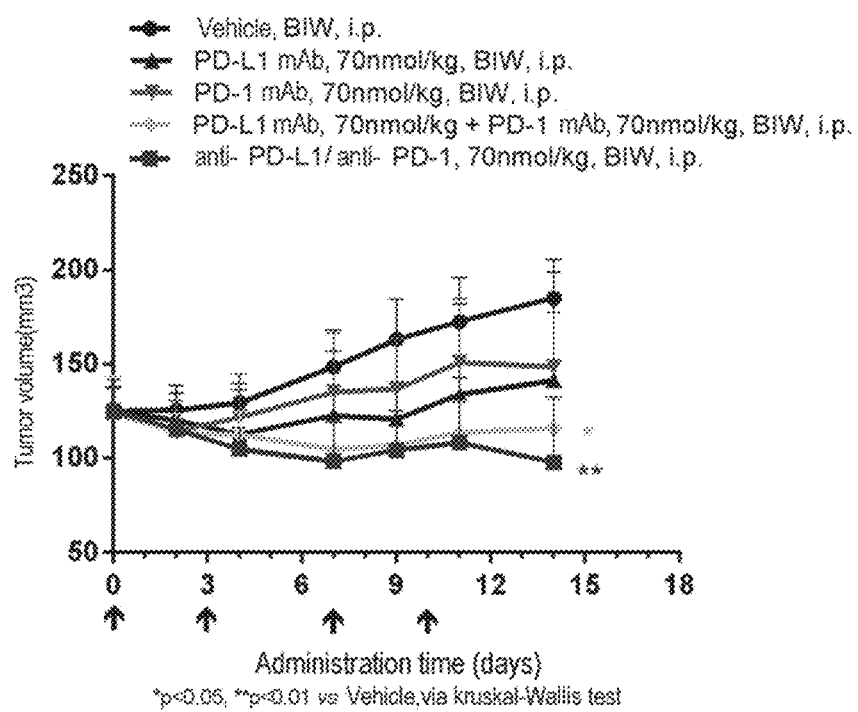
FIG. 13 illustrates the killing activity of the anti-PD-L1/anti-PD-1 heterodimeric antibody molecule on tumor cells in a mouse model.

Results are as shown in FIG. 13. Both PD-L1 mAb and PD-1 mAb exhibited anti-tumor efficacy, while the PD-L1/PD-1 heterodimeric antibody had stronger anti-tumor efficacy than the monoclonal antibodies and combinations of monoclonal antibodies. Moreover, good tumor management was exhibited even after drug withdrawal.

The invention claimed is:

1. A heterodimeric bispecific antibody, comprising a first antigen-binding functional region capable of specifically binding to PD-L1 and a second antigen-binding functional region capable of specifically binding to PD-1, wherein the bispecific antibody comprises a first Fc chain and a second Fc chain linked by one or more interchain disulfide bonds, the first Fc chain and the second Fc chain being linked respectively to the PD-L1 antigen-binding functional region and the PD-1 antigen-binding functional region by a covalent bond or a linker; or the first Fc chain and the second Fc chain being linked respectively to the PD-1 antigen-binding functional region and the PD-L1 antigen-binding functional region by a covalent bond or a linker; and the first Fc chain and the second Fc chain comprise 5 amino acid substitutions at the following positions:

the amino acid substitutions on the first Fc chain are T366L and D399R, the amino acid substitutions on the second Fc chain are L351E, Y407L and K409V;
wherein the amino acid positions are numbered according to the Kabat EU index numbering system; and
wherein the PD-L1 antigen-binding functional region comprises the amino acid sequences set forth in SEQ ID NOs: 2 and 6; and the PD-1 antigen-binding functional region comprises the amino acid sequences set forth in SEQ ID NOs: 16 and 18.

2. The heterodimeric bispecific antibody according to claim 1, wherein the Fc chains are derived from IgG.

3. The heterodimeric bispecific antibody according to claim 1, wherein the PD-L1 and PD-1 antigen-binding functional regions are Fab fragments or scFv fragments.

4. The heterodimeric bispecific antibody according to claim 1, wherein the PD-L1 and PD-1 antigen-binding functional regions are both Fab fragments.

5. The heterodimeric bispecific antibody according to claim 1, wherein one of the PD-L1 and PD-1 antigen-binding functional regions is Fab fragment, and the other is scFv.

6. The heterodimeric bispecific antibody according to claim 1, wherein the first Fc chain and the PD-L1 antigen-binding functional region linked thereto and the second Fc chain and the PD-1 antigen-binding functional region linked thereto, or the first Fc chain and the PD-1 antigen-binding functional region linked thereto and the second Fc chain and the PD-L1 antigen-binding functional region linked thereto, when present alone in the presence of a reducing agent, form homodimers at a ratio of less than 50% by weight.

7. The heterodimeric bispecific antibody according to claim 6, wherein the first Fc chain and the PD-L1 antigen-binding functional region linked thereto comprises the amino acid sequences set forth in SEQ ID NOs: 2, 4, 6 and 8; the second Fc chain and the PD-1 antigen-binding functional region linked thereto comprises the amino acid sequences set forth in SEQ ID NOs: 4, 14, 16, and 18.

8. A composition comprising the heterodimeric bispecific antibody according to claim 1 and a pharmaceutically acceptable carrier.

* * * * *

SEQUENCE LISTING

<160> NUMBER OF SEQ ID NOS: 18

<210> SEQ ID NO 1
<211> LENGTH: 306
<212> TYPE: DNA
<213> ORGANISM: Artificial Sequence
<220> FEATURE:
<223> OTHER INFORMATION: A synthetic nucleotide sequence of the anti-PD-
      L1 antibody light chain variable region

<400> SEQUENCE: 1
gacatccaga tgacccagag ccctagcagc ctgagcgcta gcgtgggcga cagggtgacc        60
atcacctgca gggccagcca ggatgtgagc accgctgtgg cctggtatca acagaagccc       120
ggcaaggccc ccaagtggta cagcgccagc ttcctgtaca gcggcgtgcc cagcagattt       180
agcggcagcg gcagcggcac cgatttcacc ctgaccatca gcagcctgca gcccgaggac       240
ttcgccacct actactgcca gcagtacctg taccatcccg ccaccttcgg ccagggcacc    300
aaggtg    306

<210> SEQ ID NO 2
<211> LENGTH: 102
<212> TYPE: PRT
<213> ORGANISM: Artificial Sequence
<220> FEATURE:
<223> OTHER INFORMATION: A synthetic amino acid sequence of the anti-PD-
      L1 antibody light chain variable region

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Trp Tyr Ser
        35                  40                  45

Ala Ser Phe Leu Tyr Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Tyr Leu Tyr His Pro Ala Thr Phe
                85                  90                  95

Gly Gln Gly Thr Lys Val
            100

<210> SEQ ID NO 3
<211> LENGTH: 330
<212> TYPE: DNA
<213> ORGANISM: Artificial Sequence
<220> FEATURE:
<223> OTHER INFORMATION: A synthetic nucleotide sequence of the anti-PD-
      L1 antibody light chain constant region

<400> SEQUENCE: 3
gagatcaagc gaactgtggc cgctccaagc gtcttcattt ttccaccctc tgacgaacag    60
ctgaagtcag ggacagcttc cgtggtctgt ctgctgaaca atttttaccc caggggaggcc    120 aaagtgcagt ggaaggtcga taacgctctg cagagcggaa attctcagga gagtgtgaca    180
gaacaggact caaaagattc cacttatagc ctgtctagta ccctgacact gtccaaggca    240
gactacgaaa agcataaagt gtatgcctgt gaggtcacac atcagggtct gtcaagcccc    300
gtcactaagt ccttcaatcg tggcgaatgc    330

<210> SEQ ID NO 4
<211> LENGTH: 110
<212> TYPE: PRT
<213> ORGANISM: Artificial Sequence
<220> FEATURE:
<223> OTHER INFORMATION: A synthetic amino acid sequence of the anti-PD-
      L1 antibody light chain constant region

<400> SEQUENCE: 4

Glu Ile Lys Arg Thr Val Ala Ala Pro Ser Val Phe Ile Phe Pro Pro
1               5                   10                  15

Ser Asp Glu Gln Leu Lys Ser Gly Thr Ala Ser Val Val Cys Leu Leu
            20                  25                  30

Asn Asn Phe Tyr Pro Arg Glu Ala Lys Val Gln Trp Lys Val Asp Asn
        35                  40                  45

Ala Leu Gln Ser Gly Asn Ser Gln Glu Ser Val Thr Glu Gln Asp Ser
        50                  55                  60

Lys Asp Ser Thr Tyr Ser Leu Ser Ser Thr Leu Thr Leu Ser Lys Ala
65                  70                  75                  80

Asp Tyr Glu Lys His Lys Val Tyr Ala Cys Glu Val Thr His Gln Gly
                85                  90                  95

Leu Ser Ser Pro Val Thr Lys Ser Phe Asn Arg Gly Glu Cys
            100                 105                 110

<210> SEQ ID NO 5
<211> LENGTH: 354
<212> TYPE: DNA
<213> ORGANISM: Artificial Sequence
<220> FEATURE:
<223> OTHER INFORMATION: A synthetic nucleotide sequence of the anti-PD-
      L1 antibody heavy chain variable region

<400> SEQUENCE: 5
gaggtgcagc tggtggagag cggaggagga ctggtgcagc tggaggatc cctgagactg        60 agctgcgccg ccagcggctt caccttcagc gacagctgga tccactgggt gagacaggcc     120
cctggcaagg gcctggaatg ggtggcctgg atctccccctt acggcggcag cacctactac     180
gccgacagcg tgaagggcag gttcaccatc agcgccgaca ccagcaagaa caccgcctac     240
ctgcagatga acagcctgag ggccgaggac accgccgtgt actactgcgc cagaagacac     300
tggcccggcg gattcgacta ctggggacag ggcaccctgg tgaccgtgag cgcc           354

<210> SEQ ID NO 6
<211> LENGTH: 118
<212> TYPE: PRT
<213> ORGANISM: Artificial Sequence
<220> FEATURE:
<223> OTHER INFORMATION: A synthetic amino acid sequence of the anti-PD-
      L1 antibody heavy chain variable region

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 7
<211> LENGTH: 990
<212> TYPE: DNA
<213> ORGANISM: Artificial Sequence
<220> FEATURE:
<223> OTHER INFORMATION: A synthetic nucleotide sequence of the anti-PD-
      L1 antibody heavy chain constant region

<400> SEQUENCE: 7

```
gcttcaacaa aaggaccttc cgtgtttcca ctggcaccct ctagtaagag tacttcagga      60
ggaaccgcag cactgggatg tctggtgaag gactacttcc cagagcccgt caccgtgtct     120
tggaacagtg gagcactgac ctccggggtc catacatttc ctgccgtgct gcagtcatcc     180
ggtctgtata gcctgagctc tgtggtcaca gtcccaagtt catccctggg cacccagaca     240
tacatctgca acgtgaatca caaaccttcc aatactaagg tcgacaagaa agtggaacca     300
aaaagctgtg ataagactca tacctgccca ccttgtcctg caccagagct gctgggaggt     360
ccaagcgtgt tcctgtttcc acccaagccc aaagacacac tgatgatttc tcgcacaccc     420
gaagtcactt gtgtggtcgt ggacgtgtcc cacgaggatc ctgaagtcaa gttcaactgg     480
tacgtggatg gcgtcgaggt gcataatgct aagaccaaac ccagagagga acagtacgcc     540
agcacctatc gcgtcgtgtc tgtcctgaca gtgctgcacc aggattggct gaacggaaag     600
gagtacaagt gcaaagtgag caacaaggcc ctgcccgctc ctatcgagaa gaccatttct     660
aaggctaaag ccagcctaga gaaccacagg tgtatacag agcctccaag tcgcgacgag     720
ctgacaaaaa accaggtctc cctgacttgt ctggtgaagg gattctaccc tagcgatatc     780
gcagtggagt gggaatctaa tgggcagcca gaaaacaatt ataagaccac ccccctgtg     840 ctggactcag atggttcctt cttttctgctg agtgtgctga ccgtggacaa gtccaggtgg     900
cagcagggga acgtcttttc ctgcagcgtg atgcatgagg ccctgcacaa tcattacaca     960
cagaaatctc tgagtctgtc accaggaaag                                      990
```

<210> SEQ ID NO 8
<211> LENGTH: 330
<212> TYPE: PRT
<213> ORGANISM: Artificial Sequence
<220> FEATURE:
<223> OTHER INFORMATION: A synthetic amino acid sequence of the anti-PD-L1 antibody heavy chain constant region

<400> SEQUENCE: 8

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                       165                 170                 175
Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Glu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Leu Ser Val Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 333
<212> TYPE: DNA
<213> ORGANISM: Artificial Sequence
<220> FEATURE:
<223> OTHER INFORMATION: A synthetic nucleotide sequence of the anti-PD-
      1 antibody light chain variable region

<400> SEQUENCE: 9
gagatcgtgc tgacccagag ccctgccaca ctgagcctga gccctggcga aagggccacc      60
ctgagctgca gggctagcaa gggcgtgagc accagcggct acagctacct gcactggtat     120
caacagaagc ccggccaggc tcctaggctg ctgatctacc tggccagcta tctggagagc     180
ggcgtgcccg ctagattcag cggaagcggc agcggcaccg acttcaccct gaccatcagc     240
agcctggagc ccgaggactt cgccgtgtac tactgccagc acagcaggga cctgcctctg     300
accttcggag gcggcaccaa ggtggagatc aag                                  333

<210> SEQ ID NO 10
<211> LENGTH: 111
<212> TYPE: PRT
<213> ORGANISM: Artificial Sequence
<220> FEATURE:
<223> OTHER INFORMATION: A synthetic amino acid sequence of the anti-PD-
      1 antibody light chain variable region

<400> SEQUENCE: 10

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
```

```
                65                  70                  75                  80
Ser Leu Glu Pro Glu Asp Phe Ala Val Tyr Tyr Cys Gln His Ser Arg
                    85                  90                  95

Asp Leu Pro Leu Thr Phe Gly Gly Gly Thr Lys Val Glu Ile Lys
                100                 105                 110
```

<210> SEQ ID NO 11
<211> LENGTH: 360
<212> TYPE: DNA
<213> ORGANISM: Artificial Sequence
<220> FEATURE:
<223> OTHER INFORMATION: A synthetic nucleotide sequence of the anti-PD-
      1 antibody heavy chain variable region

<400> SEQUENCE: 11

```
caggtgcagc tggtgcagag cggcgtggag gtgaagaagc ctggcgccag cgtgaaggtg      60
agctgcaagg ccagcggcta caccttcacc aactactaca tgtactgggt gaggcaggcc     120
cctggccaag actggagtg gatgggcggc atcaacccca gcaacggcgg caccaacttc      180
aacgagaagt tcaagaacag ggtgaccctg accaccgaca gcagcaccac caccgcctac     240
atggagctga gagcctgca gttcgacgac accgccgtgt actactgcgc caggagggac      300
tacaggttcg acatgggctt cgactactgg ggccagggca ccacagtgac cgtgtccagc     360
```

<210> SEQ ID NO 12
<211> LENGTH: 120
<212> TYPE: PRT
<213> ORGANISM: Artificial Sequence
<220> FEATURE:
<223> OTHER INFORMATION: A synthetic amino acid sequence of the anti-PD-
      1 antibody heavy chain variable region

<400> SEQUENCE: 12

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser
            115                 120
```

<210> SEQ ID NO 13
<211> LENGTH: 990
<212> TYPE: DNA
<213> ORGANISM: Artificial Sequence
<220> FEATURE:
<223> OTHER INFORMATION: A synthetic nucleotide sequence of the anti-PD-
      1 antibody heavy chain constant region

<400> SEQUENCE: 13

```
gcttcaacaa aaggaccttc cgtgtttcca ctggcaccct ctagtaagag tacttcagga      60
```

```
ggaaccgcag cactgggatg tctggtgaag gactacttcc cagagcccgt caccgtgtct    120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaacca    300
aaaagctgtg ataagactca tacctgccca ccttgtcctg caccagagct gctgggaggt    360
ccaagcgtgt tcctgtttcc acccaagccc aaagacacac tgatgatttc tcgcacaccc    420
gaagtcactt gtgtggtcgt ggacgtgtcc cacgaggatc ctgaagtcaa gttcaactgg    480
tacgtggatg gcgtcgaggt gcataatgct aagaccaaac ccagagagga acagtacgcc    540
agcacctatc gcgtcgtgtc tgtcctgaca gtgctgcacc aggattggct gaacggaaag    600
gagtacaagt gcaaagtgag caacaaggcc ctgcccgctc ctatcgagaa gaccatttct    660
aaggctaaag gccagcctag agaaccacag gtgtatacac tgcctccaag tcgcgacgag    720
ctgacaaaaa accaggtctc cctgctgtgt ctggtgaagg gattctaccc tagcgatatc    780
gcagtggagt gggaatctaa tgggcagcca gaaacaatt ataagaccac ccccctgtg    840 ctgcggtcag atggttcctt ctttctgtac agtaaactga ccgtggacaa gtccaggtgg    900
cagcagggga acgtcttttc ctgcagcgtg atgcatgagg ccctgcacaa tcattacaca    960
cagaaatctc tgagtctgtc accaggaaag                                     990
```

```
<210> SEQ ID NO 14
<211> LENGTH: 330
<212> TYPE: PRT
<213> ORGANISM: Artificial Sequence
<220> FEATURE:
<223> OTHER INFORMATION: A synthetic amino acid sequence of the anti-PD-
      1 antibody heavy chain constant region

<400> SEQUENCE: 14
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Arg Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 321
<212> TYPE: DNA
<213> ORGANISM: Artificial Sequence
<220> FEATURE:
<223> OTHER INFORMATION: A synthetic nucleotide sequence of the anti-PD-
      1 antibody light chain variable region

<400> SEQUENCE: 15
gatatcgttc tcacccagtc tccagccacc ctgtctgtga ctccaggaga tagcgtcagt     60
ctttcctgca gggccaacca aagtattagc aacaacctac actggtatca acaaagatca    120
catgagtctc cgaggcttct catcagattt gcttcccagt ccatctctgg atcccctcc    180 aggttcagtg gcagtggatc aggacagat ttcactctca gtatcaacag tgtggagact    240
gaagattttg gaatgtattt ctgtcaacag agtgacaact ggcctctcac gttcggtgct    300
gggaccaagc tggagatcaa g                                              321

<210> SEQ ID NO 16
<211> LENGTH: 107
<212> TYPE: PRT
<213> ORGANISM: Artificial Sequence
<220> FEATURE:
<223> OTHER INFORMATION: A synthetic amino acid sequence of the anti-PD-
      1 antibody light chain variable region

<400> SEQUENCE: 16

Asp Ile Val Leu Thr Gln Ser Pro Ala Thr Leu Ser Val Thr Pro Gly
1               5                   10                  15

Asp Ser Val Ser Leu Ser Cys Arg Ala Asn Gln Ser Ile Ser Asn Asn
            20                  25                  30

Leu His Trp Tyr Gln Gln Arg Ser His Glu Ser Pro Arg Leu Leu Ile
        35                  40                  45

Arg Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asp Asn Trp Pro Leu
                85                  90                  95
```

```
Thr Phe Gly Ala Gly Thr Lys Leu Glu Ile Lys
            100                 105
```

<210> SEQ ID NO 17
<211> LENGTH: 351
<212> TYPE: DNA
<213> ORGANISM: Artificial Sequence
<220> FEATURE:
<223> OTHER INFORMATION: A synthetic nucleotide sequence of the anti-PD-
      1 antibody heavy chain variable region

<400> SEQUENCE: 17

```
gaggttcagc tgcaggagtc tggggggaggc ttagtgaagc ctggagggtc cctgaaactc      60
tcctgtgcag cctctggatt cactttcagt agctatggca tgtcttgggt tcgccagact     120
ccggagaaga ggctggagtg ggtcgcaagc attagtggtg gtggtcgtta tacctactat     180
ccagacagta tgaaggggcg attcaccatc tccagagaca atgccaagaa caacctgcac     240
ctgcaaatga gcagtctgag gtctgaggac acggccttgt attactgtgt ctatgaatat     300
ttttatacta tggactactg gggtcaagga acctcagtca ccgtctcctc a              351
```

<210> SEQ ID NO 18
<211> LENGTH: 117
<212> TYPE: PRT
<213> ORGANISM: Artificial Sequence
<220> FEATURE:
<223> OTHER INFORMATION: A synthetic amino acid sequence of the anti-PD-
      1 antibody heavy chain variable region

<400> SEQUENCE: 18

```
Glu Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Ser Ile Ser Gly Gly Gly Arg Tyr Thr Tyr Tyr Pro Asp Ser Met
    50                  55                  60

Lys Gly Arg Phe Thr Ile Ser Arg Asp Asn Ala Lys Asn Asn Leu His
65                  70                  75                  80

Leu Gln Met Ser Ser Leu Arg Ser Glu Asp Thr Ala Leu Tyr Tyr Cys
                85                  90                  95

Val Tyr Glu Tyr Phe Tyr Thr Met Asp Tyr Trp Gly Gln Gly Thr Ser
            100                 105                 110

Val Thr Val Ser Ser
        115
```